US012740775B2

(12) United States Patent
Sauer et al.

(10) Patent No.: US 12,740,775 B2
(45) Date of Patent: Sep. 22, 2026

(54) STERNAL ASCENDER APPARATUS

(71) Applicant: LSI Solutions, Inc., Victor, NY (US)

(72) Inventors: Jude S. Sauer, Pittsford, NY (US); Matthew David DeClerck, Greece, NY (US); Angelo John Martellaro, Victor, NY (US); Benjamin James Boseck, Canandaigua, NY (US); Matthew Wrona, Fairport, NY (US); Alexander G. Murashko, Webster, NY (US)

(73) Assignee: LSI Solutions, Inc., Victor, NY (US)

( * ) Notice: Subject to any disclaimer, the term of this patent is extended or adjusted under 35 U.S.C. 154(b) by 638 days.

(21) Appl. No.: 18/108,167

(22) Filed: Feb. 10, 2023

(65) Prior Publication Data

US 2023/0190254 A1 Jun. 22, 2023

Related U.S. Application Data

(63) Continuation-in-part of application No. 16/999,838, filed on Aug. 21, 2020, now Pat. No. 11,666,317.

(60) Provisional application No. 62/889,690, filed on Aug. 21, 2019, provisional application No. 62/916,591, filed on Oct. 17, 2019, provisional application No. 62/989,044, filed on Mar. 13, 2020, provisional application No. 63/309,234, filed on Feb. 11, 2022.

(51) Int. Cl.
*A61B 17/02* (2006.01)

(52) U.S. Cl.
CPC .. *A61B 17/0218* (2013.01); *A61B 2017/0237* (2013.01)

(58) Field of Classification Search
CPC . A61B 17/02; A61B 17/0218; A61B 17/0237; A61B 17/0281
See application file for complete search history.

(56) References Cited

U.S. PATENT DOCUMENTS

| | | | | |
|---|---|---|---|---|
| 380,081 | A * | 3/1888 | Bowman | B65B 13/025 254/230 |
| 1,919,455 | A | 7/1933 | Wilson | |
| 3,196,865 | A | 7/1965 | Rose | |
| 5,052,373 | A * | 10/1991 | Michelson | A61B 17/0206 600/234 |
| 5,167,223 | A * | 12/1992 | Koros | A61B 17/0206 600/234 |

(Continued)

OTHER PUBLICATIONS

PCT Search Report and Written Opinion for PCT/US2020/47440, International filing date Aug. 21, 2020, 9 pages, mailed Feb. 10, 2021.

(Continued)

*Primary Examiner* — Nicholas W Woodall
(74) *Attorney, Agent, or Firm* — Michael E. Coyne

(57) ABSTRACT

A sternal elevator apparatus is disclosed. The sternal elevator may include a panel, a support beam traversing the panel, and a post coupled to a proximal end of the panel. The apparatus may also include an indicator handle coupled to the sternal elevator, an actuator drive pivotably coupled to the indicator handle, and a housing movably coupled to the actuator drive. The sternal elevator apparatus may have an actuator drive incorporating a linear rack. The housing further may include a cylindrical gear where the cylindrical gear is engaged with the linear rack.

8 Claims, 21 Drawing Sheets

(56) References Cited

U.S. PATENT DOCUMENTS

| | | | | |
|---|---|---|---|---|
| 5,795,291 | A * | 8/1998 | Koros | A61B 17/02 600/231 |
| 5,846,191 | A | 12/1998 | Wells et al. | |
| 5,893,831 | A * | 4/1999 | Koros | A61B 17/02 600/222 |
| 6,042,542 | A * | 3/2000 | Koros | A61B 17/02 600/231 |
| 7,909,846 | B1 | 3/2011 | Taylor et al. | |
| 8,974,381 | B1 * | 3/2015 | Lovell | A61B 90/30 600/222 |
| 9,113,853 | B1 * | 8/2015 | Casey | A61B 90/30 |
| 9,335,782 | B2 * | 5/2016 | Koros | G05G 1/082 |
| 2005/0148824 | A1 | 7/2005 | Morejohn et al. | |
| 2005/0159651 | A1 | 7/2005 | Raymond et al. | |
| 2007/0161865 | A1 * | 7/2007 | Fakhrai | A61B 17/0206 600/231 |
| 2007/0238932 | A1 | 10/2007 | Jones et al. | |
| 2010/0312069 | A1 | 12/2010 | Sutherland et al. | |
| 2016/0000419 | A1 * | 1/2016 | Weisshaupt | A61B 17/0206 600/225 |
| 2017/0239048 | A1 | 8/2017 | Goldfarb et al. | |
| 2020/0015801 | A1 | 1/2020 | Sauer | |

OTHER PUBLICATIONS

Chanoit et al., Retraction mechanics of Finochietto-style self-retaining thoracic retractors, BioMedical Engineering OnLine, 18, Article No. 45, 35 pages, Jul. 19, 2021.

Extended European Search Report for EP Application No. 20855514.4, dated Jul. 4, 2023, 10 pages.

* cited by examiner 238
278
228
297
282
T
228
278
238
282
298
238
284
264
286
288
297
280
290
294
278
296
228
282
292
266
x
y

STERNAL ASCENDER APPARATUS

CROSS-REFERENCE TO RELATED APPLICATIONS

This application is a continuation-in-part application claiming priority to U.S. patent application Ser. No. 16/999,838, filed Aug. 21, 2020, which claims priority to each of U.S. Provisional Patent Application No. 62/889,690, filed Aug. 21, 2019, U.S. Provisional Patent Application No. 62/916,591, filed Oct. 17, 2019, and U.S. Provisional Patent Application No. 62/989,044, filed Mar. 13, 2020, each of which is hereby incorporated by reference in its entirety. This application also claims the benefit of U.S. Provisional Patent Application No. 63/309,234, filed Feb. 11, 2022, which is hereby incorporated by reference in its entirety.

FIELD

The claimed invention relates to minimally invasive surgical devices, and more specifically to a surgical device used in increasing operable space during minimally invasive surgical procedures.

BACKGROUND

Minimally invasive surgical approaches are gaining increased interest in relation to coronary procedures. Coronary revascularization procedures such as the grafting of the internal thoracic artery (ITA) has shown superior long-term patency and improved patient outcome in coronary artery bypass graft (CABG) surgeries. While conventional approaches to ITA harvesting have included median sternotomy or multiple thoracoports, a minimally invasive approach is desirable. A minimally invasive procedure related to revascularization using either the left or right internal thoracic artery (ITA), or the left or right internal mammary artery (IMA) may utilize access to the ITAs via sub-xiphoid access, where increased surgical space is gained by accessing the internal thoracic arteries via incision at the subxiphocostal region.

Upon harvesting either the left internal thoracic artery (LITA) or the right internal thoracic artery (RITA) anastomoses to the left anterior descending (LAD) coronary artery and to the right coronary artery (RCA), respectively, can be performed without cardiopulmonary bypass (CPB). A significant advantage of this approach is that a perfectly harvested ITA graft can be perfectly anastomosed to the usual site on the LAD artery, or onto the RCA artery. A minimally invasive ITA harvesting procedure involving sub-xiphoid access also results in superior cosmetic results, is reasonably painless, and the arterial grafting can be accomplished on the beating heart. Recent approaches of minimally invasive ITA harvesting surgical techniques have been shown to result in increased effective length of ITA bypasses, reduced operation times, and improved patient recovery.

While less invasive surgical approaches for ITA harvesting and CABG have shown promise, visualization, maintenance of insufflation, and distal suturing of a coronary anastomosis in totally endoscopic coronary artery bypass grafting on the beating heart is technically demanding. There is a need for larger working spaces to accommodate an increased range of motion during surgical procedures, as well as room for additional surgical tools, such as endoscopes, suturing tools, and the like. However, achieving an increased working space should ideally preserve chest wall integrity and avoid CPB. Likewise, a minimally invasive surgical approach should not compromise the reliability of a cardiac repair.

Therefore, there exists a need for minimally invasive surgical devices and methodology applicable to ITA harvesting and other surgical procedures such as epicardial lead placement and others that increase operable space for harvesting and anastomosis and other surgical procedures, reduce operating time, and improve patient outcome during minimally invasive cardiac procedures and other surgical procedures.

Figure 1:
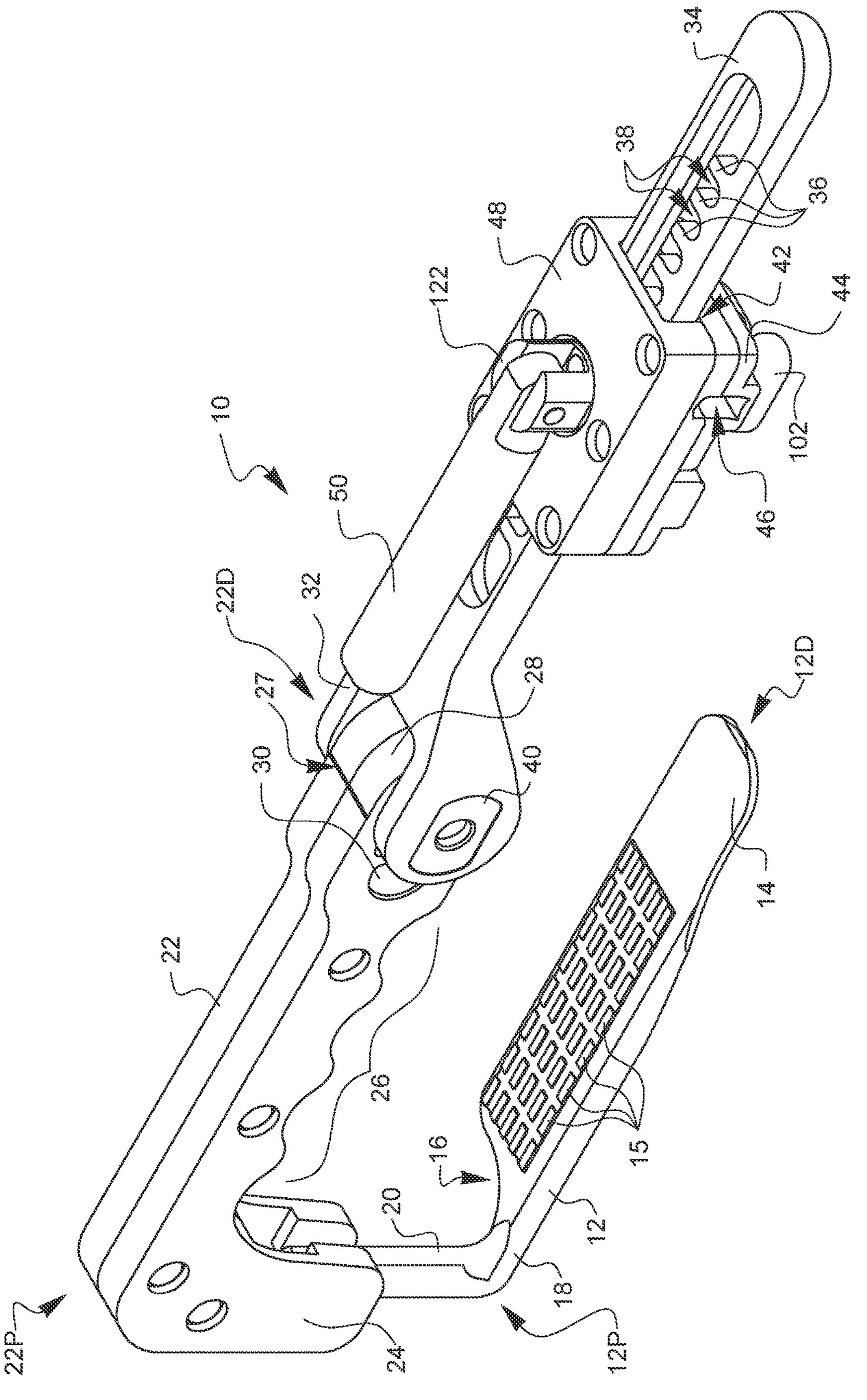
FIG. 1 is a top-front-right perspective view of one embodiment of a sternal ascender apparatus with a right sternal ascender attached.

It will be appreciated that for purposes of clarity and where deemed appropriate, reference numerals have been repeated in the figures to indicate corresponding features, and that the various elements in the drawings have not necessarily been drawn to scale in order to better show the features.

SUMMARY

A sternal ascender apparatus is disclosed. The sternal ascender may include a panel, a support beam traversing the panel, and a post coupled to a proximal end of the panel. The apparatus may also include an indicator handle coupled to the sternal ascender, an actuator drive pivotably coupled to the indicator handle, and a housing movably coupled to the actuator drive. The sternal ascender apparatus may have an actuator drive incorporating a linear rack. The housing further may include a cylindrical gear where the cylindrical gear is engaged with the linear rack.

Another sternal ascender apparatus is disclosed. The sternal ascender may include a panel having a plurality of textural features, a support beam traversing the panel, and a post coupled to a proximal end of the panel. The apparatus may also include an indicator handle removably coupled to the sternal ascender, an actuator drive pivotably coupled to the indicator handle having a linear rack, and a housing movably coupled to the actuator drive having a cylindrical gear and two instrument adapters.

DETAILED DESCRIPTION

FIG. 1 is a perspective view of one embodiment of a sternal ascender apparatus with a right sternal ascender attached. An embodiment of a sternal ascender apparatus 10 is shown in FIG. 1, with a right sternal ascender 12 installed therein. The right sternal ascender 12 defines a panel 14, the panel 14 having several textural features 15 configured to provide an atraumatic yet firm grip on the underside of a ribcage when the sternal ascender assembly 10 is in use in a minimally invasive surgical procedure. The panel 14 of the right sternal ascender 12 also defines a notch 16 and has a support beam 18 on the underside of the panel 14 The right sternal ascender 12 has a mounting post 20 on a proximal end 12P. The mounting post 20 is coupled to a proximal end 22P of an indicator handle 22 at the end of the mounting portion 24 of the indicator handle 22. The right sternal ascender 12 is coupled by reversible means such that the right sternal ascender 82 may be easily removed and replaced with a left sternal ascender, which is not shown in this view. The term ascender may be used interchangeably with the term elevator or lifter, as they equivalently describe the intended function of the ascender and associated apparatus. This coupling means will be described in further detail later. One alternate example of a coupling method is using a set screw, although others may be known to those skilled in the arts. The indicator handle 22 further defines a grip 26 in the underside of the indicator handle 22, which is configured for an ergonomic gripping feature for the comfort of use by a surgeon. At a distal end 22D of the indicator handle 22 is a connection end 28 and a pressable switch 30. Towards the distal end 22D of the indicator handle 22 is a depth indication mark 27, which is vertically aligned with the distal end 12D of the right sternal ascender 12. The connection end 28 is a coupling point that accepts a corresponding connection end 32 on a linear rack or linear actuator gear 34 by way of mating with the connection end 28 and is pivotably attached by joining a pivot pin 40 or alternatively by other attachment means into a hole or other attachment means not shown in this view. The pressable switch 30 can be pressed or actuated to defeat a pawl that is located inside the indicator handle 22, but not shown in this view. The pawl interfaces with a fixed indexing gear located inside the connection end 32 portion of the linear actuator gear 34. This will be discussed later in more detail in regard to FIGS. 2A-2E. The pawl defines a spring or biasing element to bias, while at rest, one or more teeth defined by the pawl toward the fixed indexing gear, which is not shown in this view but is coupled to the connection end 32 of the linear actuator gear 34. When the one or more teeth on the pawl intermesh with one or more corresponding teeth or other locking feature defined by the fixed indexing gear, this locks the angular position of the linear actuator gear 34 relative to the position of the indicator handle 22. When switch 30 is pressed or actuated, the pawl is defeated and temporarily pushed away from the fixed indexing gear, allowing free angular movement of the linear actuator gear 34 relative to the indicator handle 22. Releasing the switch 30, re-engages the pawl and the fixed indexing gear to once again interface and lock the angular position of the linear actuator gear 34 relative to the indicator handle 22 that it was in when the switch 30 was released.

The linear actuator gear 34 further defines several teeth 36 and several recesses 38 that engage a cylinder gear 122. The linear actuator gear 34 fits through an actuator slot 42 in a dual side instrument adapter 44. The dual side instrument adapter 44 defines a first adapter channel 46 and a second adapter channel, not visible here, on the opposite side. The dual side instrument adapter 44 also defines several securing mechanisms 100, 102 for locking the dual side instrument adapter 44 into a surgical equipment holder on each side. Once the dual side instrument adapter 44 is attached on each side to a surgical equipment holder, it can be positioned over a patient by bridging two surgical equipment holders across a surgical table. Other embodiments may only have a single adapter channel for mounting onto a single surgical equipment holder. The dual side instrument adapter 44 includes an upper rack housing 48 which holds the cylinder gear 122. A handle or swivel bar 50 is coupled to the cylinder gear 122. Turning the handle 50 rotates the cylinder gear 122 and thereby moves the linear actuator gear 34 back and forth relative to the dual side instrument adapter 44, thereby forming an actuator drive. In this embodiment, the sternal ascender assembly 10 is inserted into an incision below the sub-xiphoid of a patient undergoing a minimally invasive surgical procedure, such as an ITA harvesting procedure or other surgical procedure in which increased access space below the sub-xyphoid process is advantageous. The panel 14 of the right sternal ascender 12 can be used to enable lifting the ribcage, thereby increasing space in the subxiphoid area. One feature of the sternal ascender assembly 10 is that the length of the distal end 22D of the indicator handle 22 is substantially the same as the length of the right sternal ascender 12 panel 14, which provides the surgeon with a visible indication, along with the depth indication mark 27 of how far the right sternal ascender 12 or the right sternal ascender (if installed into the sternal ascender apparatus 10) has been inserted into the subxiphoid cavity of the patient. The distal end 22D of the indicator handle 22 is substantially aligned with a distal end 12D of the sternal ascender 12. The indicator handle 22 is also substantially parallel to the panel 14 of the right sternal ascender 12 or the panel of a right sternal ascender. Once the sternal ascender apparatus or assembly 10 is inserted into the subxiphoid cavity, the sternal ascender assembly 10 is attached to one or more surgical equipment holders, enabling stability of force throughout a minimally invasive surgical procedure. Further adjustments to the position of the sternal ascender assembly 10 may then be made by pivoting about the coupling joint of the indicator handle 22 and the linear actuator gear 34. The sternal ascender assembly 10 can be further adjusted by rotating the swivel bar 50 and actuating the linear actuator gear 34 in a distal direction. This operation will be discussed in further detail later.

Figure 2A:
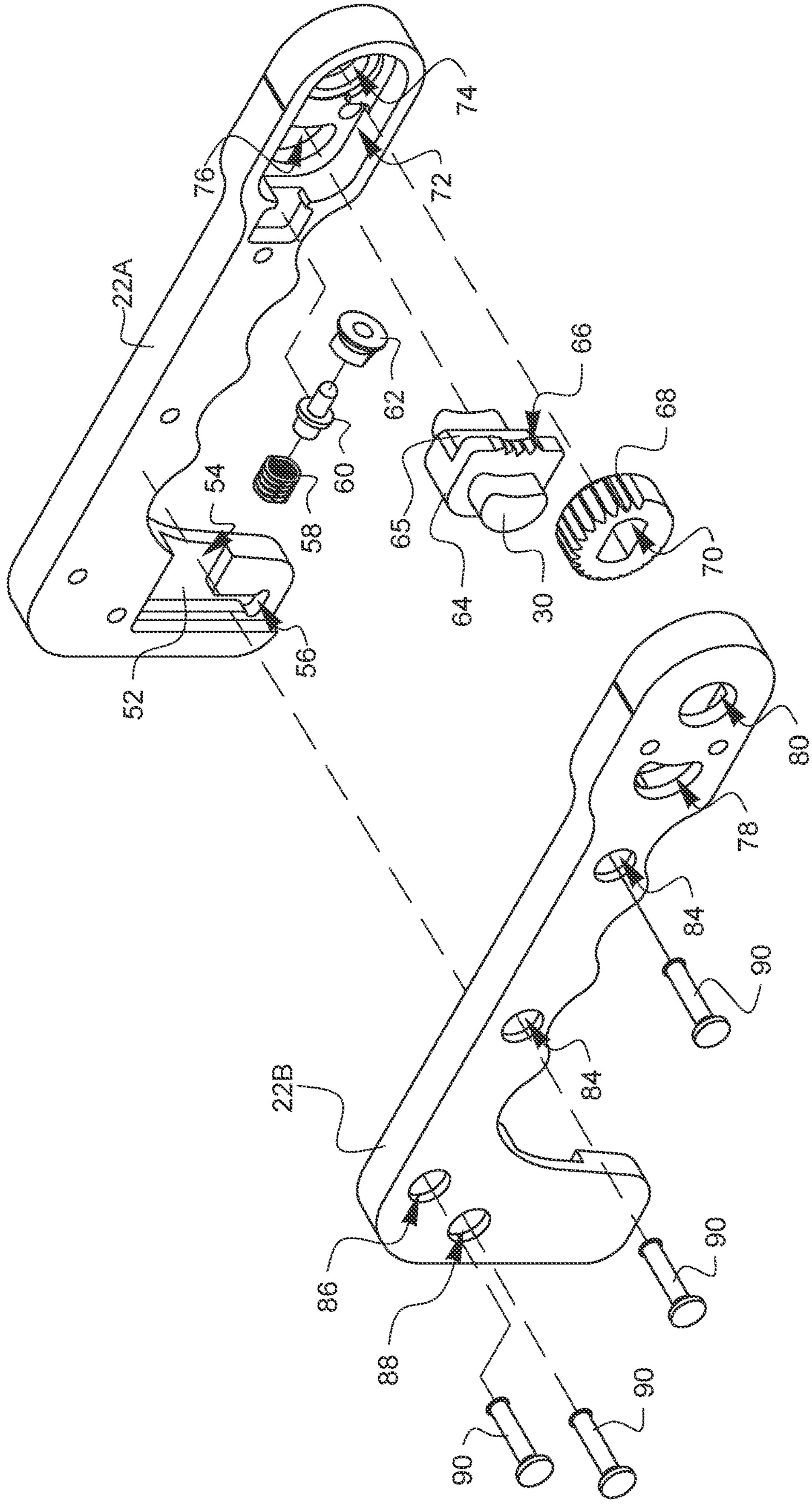
FIGS. 2A-2E is a series of exploded views illustrating the apparatus of the sternal ascender apparatus of FIG. 1.

FIGS. 2A-2E is a series of exploded views illustrating the assembly of the sternal ascender apparatus of FIG. 1. As illustrated in FIG. 2A, a first handle half 22A defines a recess or channel 52 having a mounting slot 54 and a seat 56. The mounting slot 54 and seat 56 defined by the channel 52, also referred to as a t-slot based on the general shape thereof, are configured to removably receive an alignment key on the post of either a left or right sternal ascender. A second handle half 22B also defines a corresponding recess, not shown in this view. The first handle half 22A also defines a second recess 72 at an opposite end and a gear recess 74 and hole 76. The second handle half 22B also defines a corresponding recess, not shown in this view. The second recess 72 is configured to receive and hold a spring 58, spring plunger 60, and plunger housing 62, which are first assembled together. A pawl gear 64 having gears 66 and an ungeared portion 65 and a fixed indexing gear or a pivot gear 68 having a gear keyway 70 are placed into hole 76 and held in gear recess 74, respectively, on the first handle half 22A. The pawl gear 64 is held against the spring 58, spring plunger 60, and plunger housing 62 assembly such that the pawl gear 64 is biased against the pivot gear 68 until the pawl gear 64 is depressed to slide the pawl gear 64 so that the gears 66 are disengaged from the pivot gear 68 such that it interfaces with the ungeared portion 65 of the pawl gear 64, thus allowing free rotation or pivoting of the pivot gear 68. When the pawl gear 64 is released, the gears 66 relock with the pivot gear 68 preventing further pivoting or rotation of the pivot gear 68. The second handle half 22B is then placed over the first handle half 22A and fastened using several rivets 90 which are placed and fixed into holes 84, 86, 88 on the second handle half 22B. While holes and rivets are used here to fixedly attach the handle halves 22A, 22B together, welding, adhesives or other means known to those skilled in the art may also be employed.

Figure 2B:
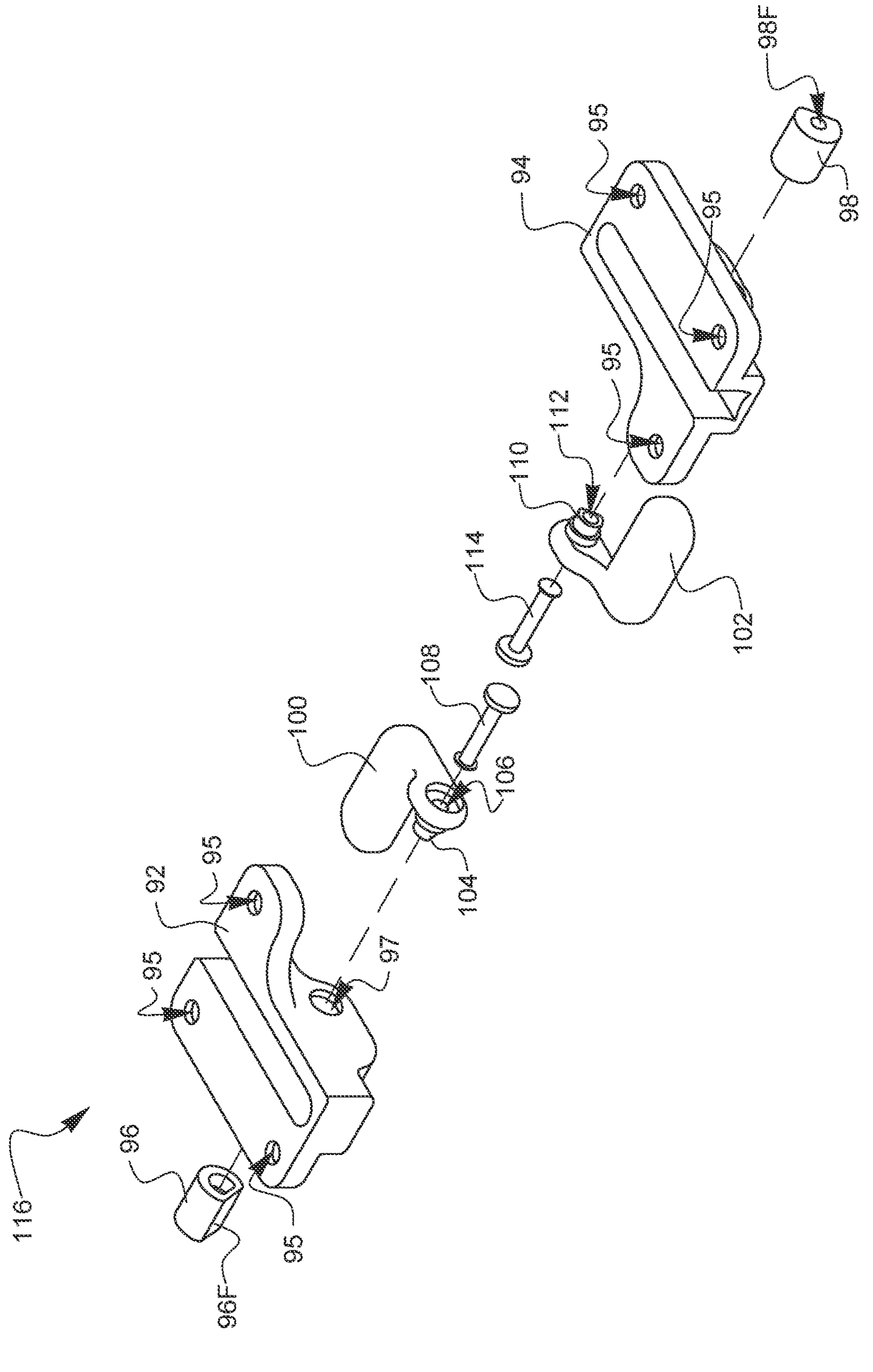

FIG. 2B illustrates that the dual side instrument adapter 44 of the sternal ascender apparatus 10 may include an instrument adapter assembly 116. The instrument adapter assembly 116 may include a first adapter housing 92 having several holes 95 and side hole 97 is assembled by placing a first cam 96 having a flat 96F into hole 97. A first lever lock 100 having a key 104 is placed into hole 97 and into the first cam 96 such that rotating the first lever lock 100 will also rotate the first cam 96 within hole 97. The first lever lock 100 is pivotably attached to the first adapter housing 92 with the use of rivet 108 being placed into channel 106 on the first lever lock 100. The instrument adapter assembly 116 may also include a second adapter housing 94 having several holes 95 and side hole, not visible here, is assembled by placing a second cam 98 having a flat 98F into hole 97. A second lever lock 102 having a key 110 is placed into a hole on the second adapter housing 94 and into the second cam 98 such that rotating the second lever lock 102 will also rotate the second cam 98 within the hole in the second adapter housing 94. The second lever lock 102 is pivotably attached to the second adapter housing 94 with the use of rivet 114 being placed into channel 112 on the second lever lock 102.

Figure 2C:
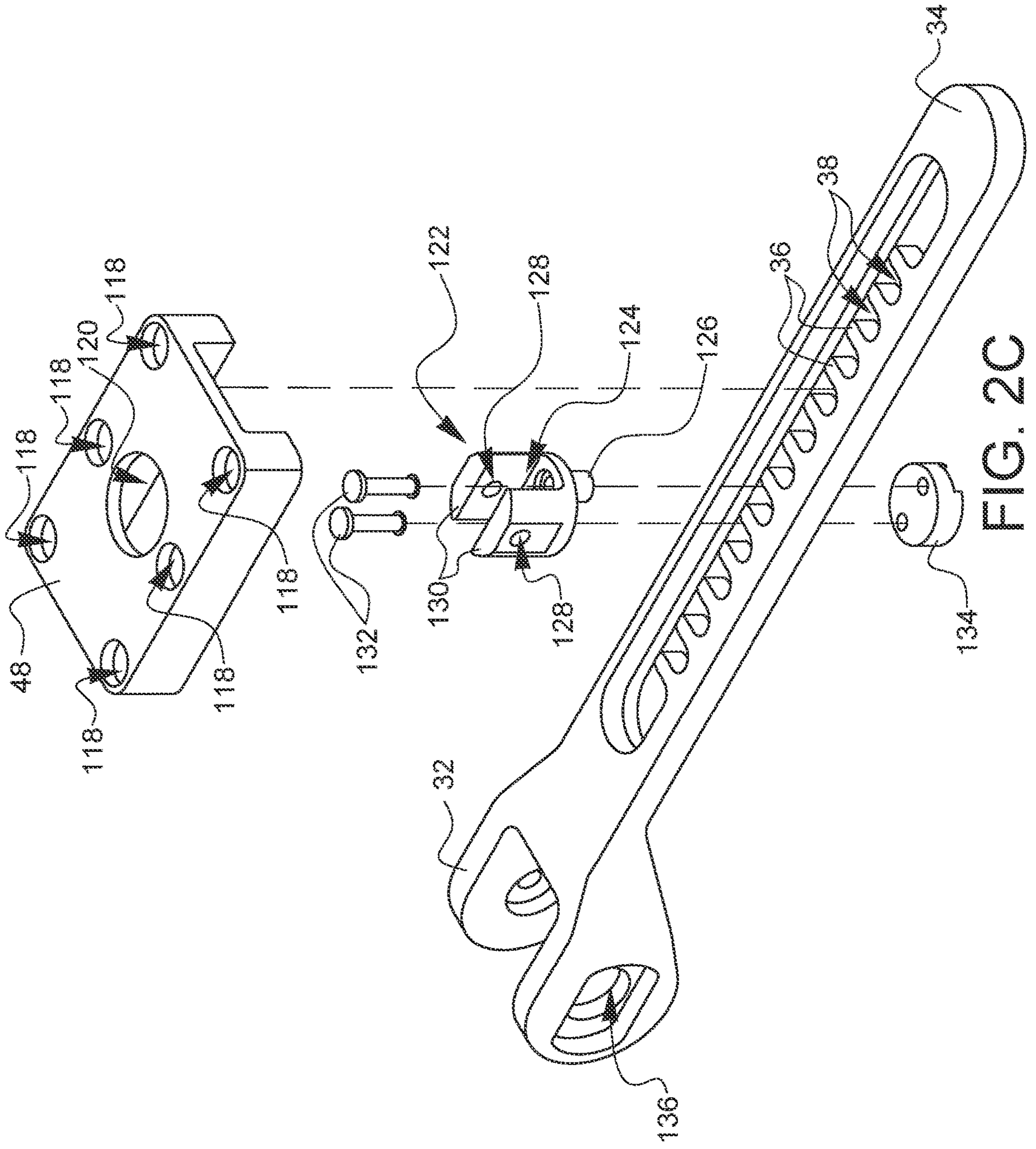
Figure 2D:
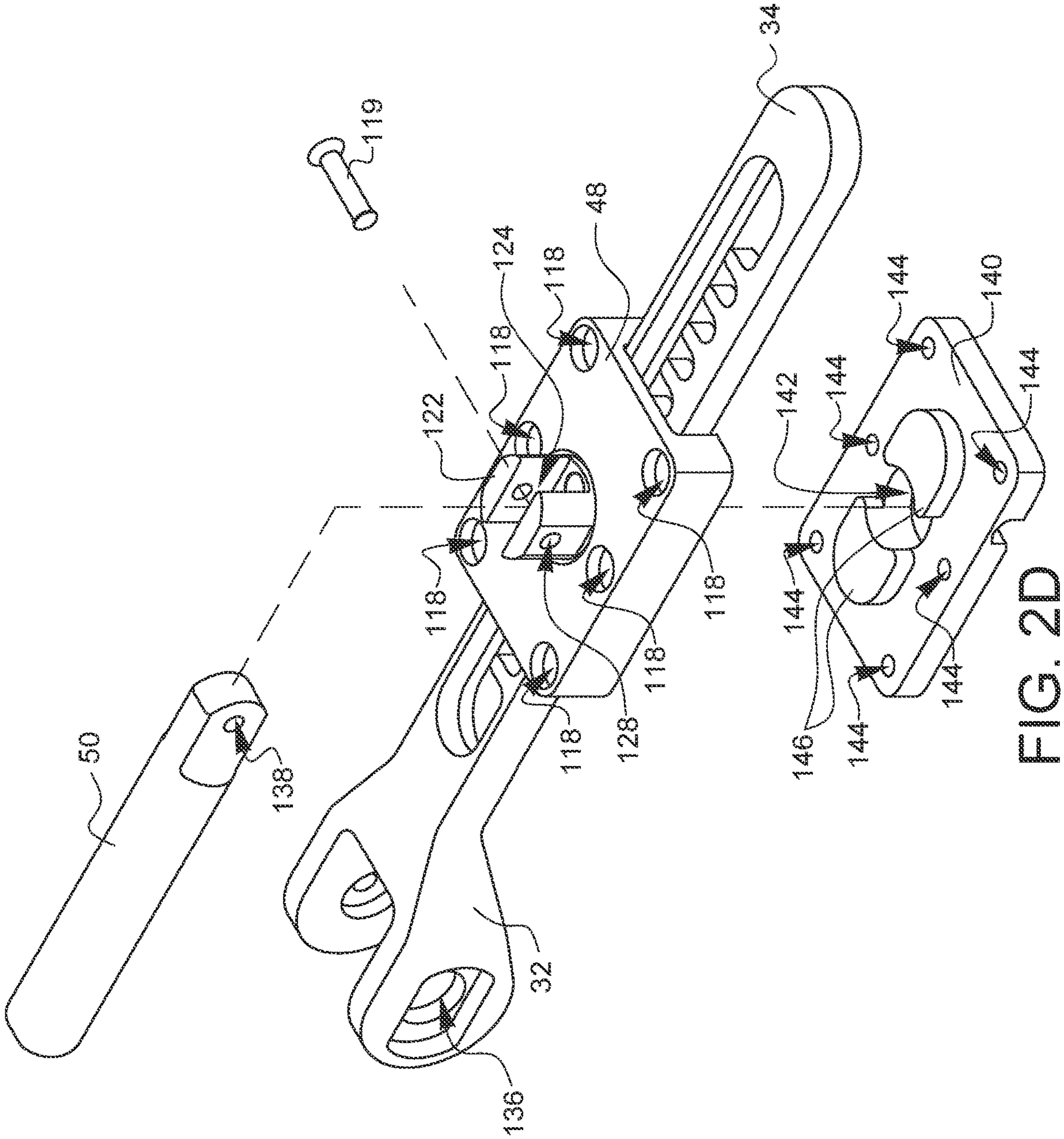
Figure 2E:
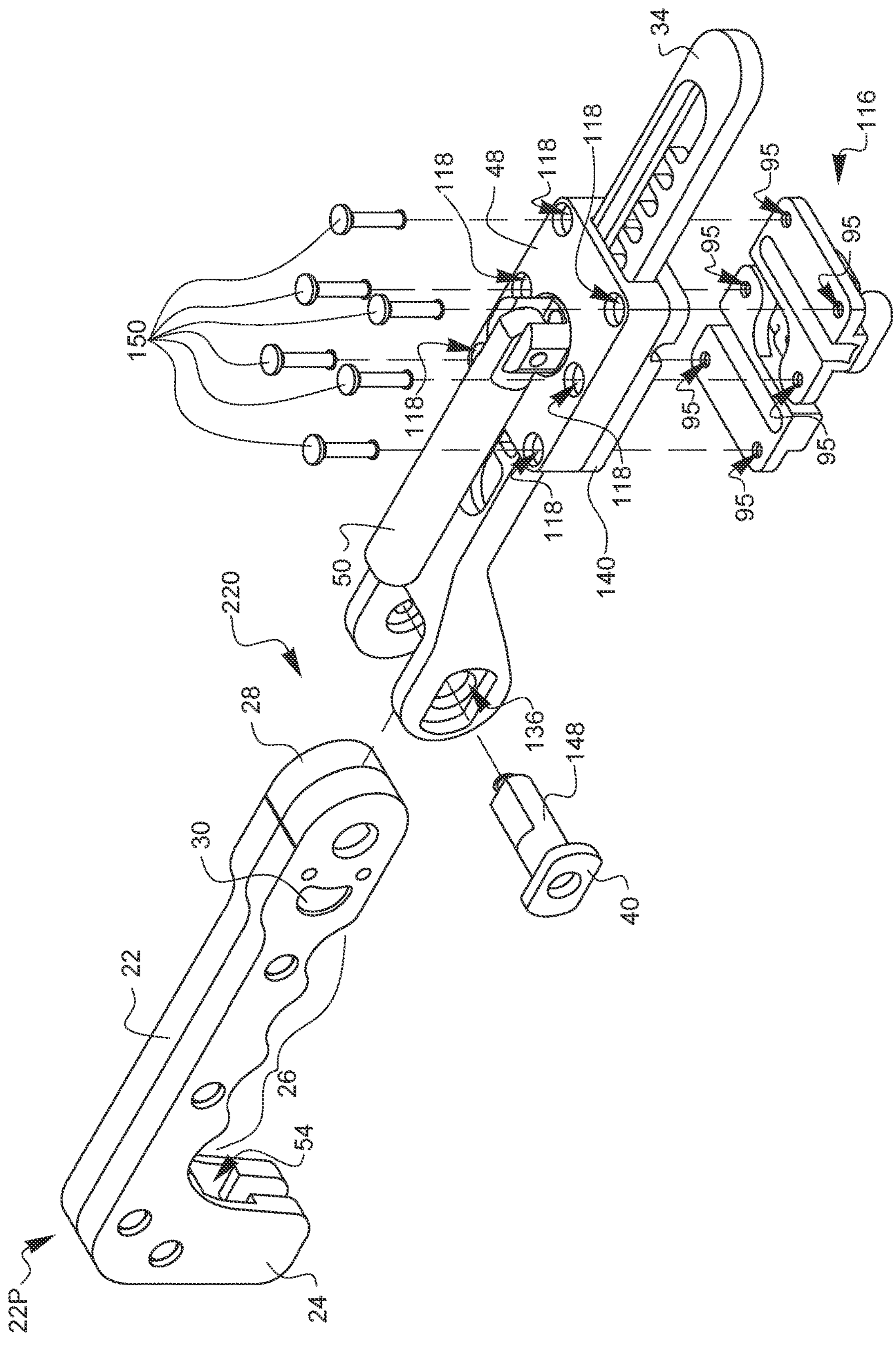

FIG. 2C continues the assembly of the sternal ascender apparatus 10 focusing on the linear actuator gear 34. The linear actuator gear 34, having a connection end 32 which further defines a hole 136 and several teeth 36 with several recesses 38 positioned therebetween. A cylinder gear 122 defines two sides 130, a side channel 128 on either side 130, a slot 124, and two posts 126, one of which is visible here, is placed into the linear actuator gear 34 with the two posts 126 held in two adjacent recesses 38. A drive bottom 134 is fixed with two rivets 132 onto the two posts 126 of the cylinder gear 122 on the opposite side of the linear actuator gear 34. Once fully assembled, the cylinder gear 122 is rotated in a clockwise or counterclockwise direction this thereby moves the linear actuator gear back and forth forming an actuator drive. As the cylinder gear 122 is rotated, the first pinion or post 126 will rotate out of a recess 38 on the linear actuator gear 34 and outward while the second pin driver (not visible here) remains in a second recess 38 and rotates within the second recess 38. The first post 126 will rotate into a third recess 38, past the second recess 38 thus translating rotational motion into linear motion and moving the linear actuator gear 34 relative to the upper rack housing 48. Performing this operation in the reverse will move the actuator gear 34 in the reverse direction. The upper rack housing 48 has a central opening 120 and several holes 118 is then placed over the linear actuator gear 34 and cylinder gear 122 so that the cylinder gear 122 protrudes from the central opening 120 of the upper rack housing 48 and the upper rack housing 48 is able to slide along the linear actuator gear 34 (or the linear actuator gear 34 is able to displace relative to the upper rack housing 48) as the cylinder gear 122 is rotated. FIG. 2D illustrates the handle 50 being placed into the cylinder gear 122 between the two sides 130 and held in place by placing a rivet 119 through the side channels 128 on the cylinder gear 122 and through the hole 138 on the swivel bar 50. The dual side instrument adapter 144 also includes a middle rack housing 140 having a central hole 142, several holes 144, and two housing inserts 146 is placed onto the bottom of the linear actuator gear 34 to align with the upper rack housing 48. The holes 118 on the upper rack housing 48 are aligned with the holes 144 on the middle rack housing 140. The two housing inserts 146 are configured to hold captive and allow free rotation of the drive bottom 134 of the cylinder gear 122. The handle or swivel bar 50 is used to swivel and rotate the cylinder gear 122 during operation. The assembly of the sternal ascender apparatus 10 is completed in FIG. 2E by inserting the distal end 22D of the indicator handle 22 into the linear actuator gear 34. The pivot pin 40 is inserted into hole 136 with the pivot pin post 148 interlocking into the gear keyway 70 of the pivot gear 68, the function of which was illustrated in FIG. 2A. The instrument adapter assembly 116 shown and described in regard to FIG. 2B is placed onto the bottom of the middle rack housing 140 and holes 95 in the instrument adapter assembly 116 are aligned with the corresponding 118 holes in the upper rack housing 48. Several rivets 150 are then placed into the holes 118 to fixedly join the instrument adapter assembly 116 to the middle rack housing 140 and upper rack housing 48, thereby forming an embodiment of the dual side instrument adapter 44.

Figure 3:
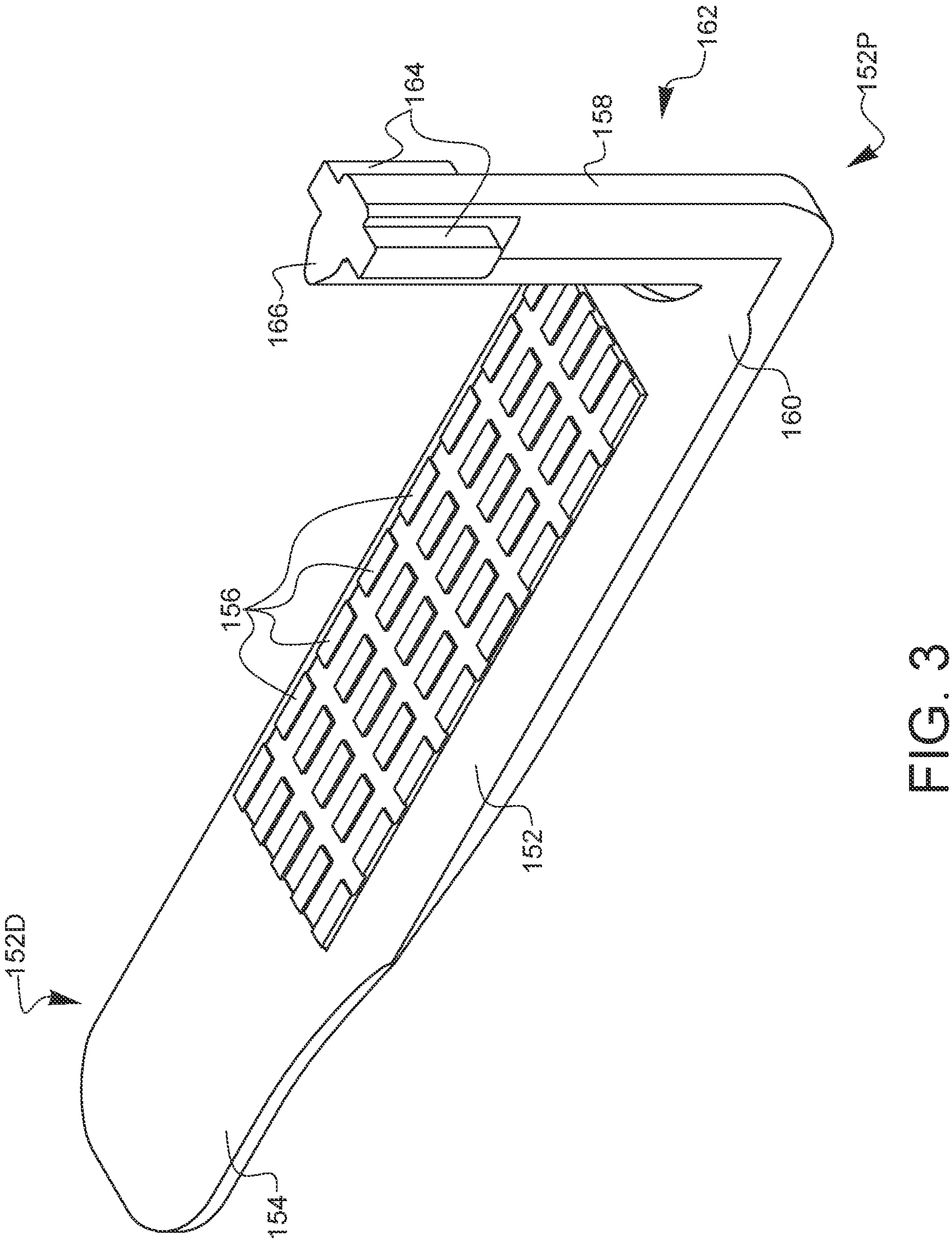
FIG. 3 is a perspective view of a left sternal ascender.
Figures 4A, 4B, 4C, 4D, 4E, 4F:
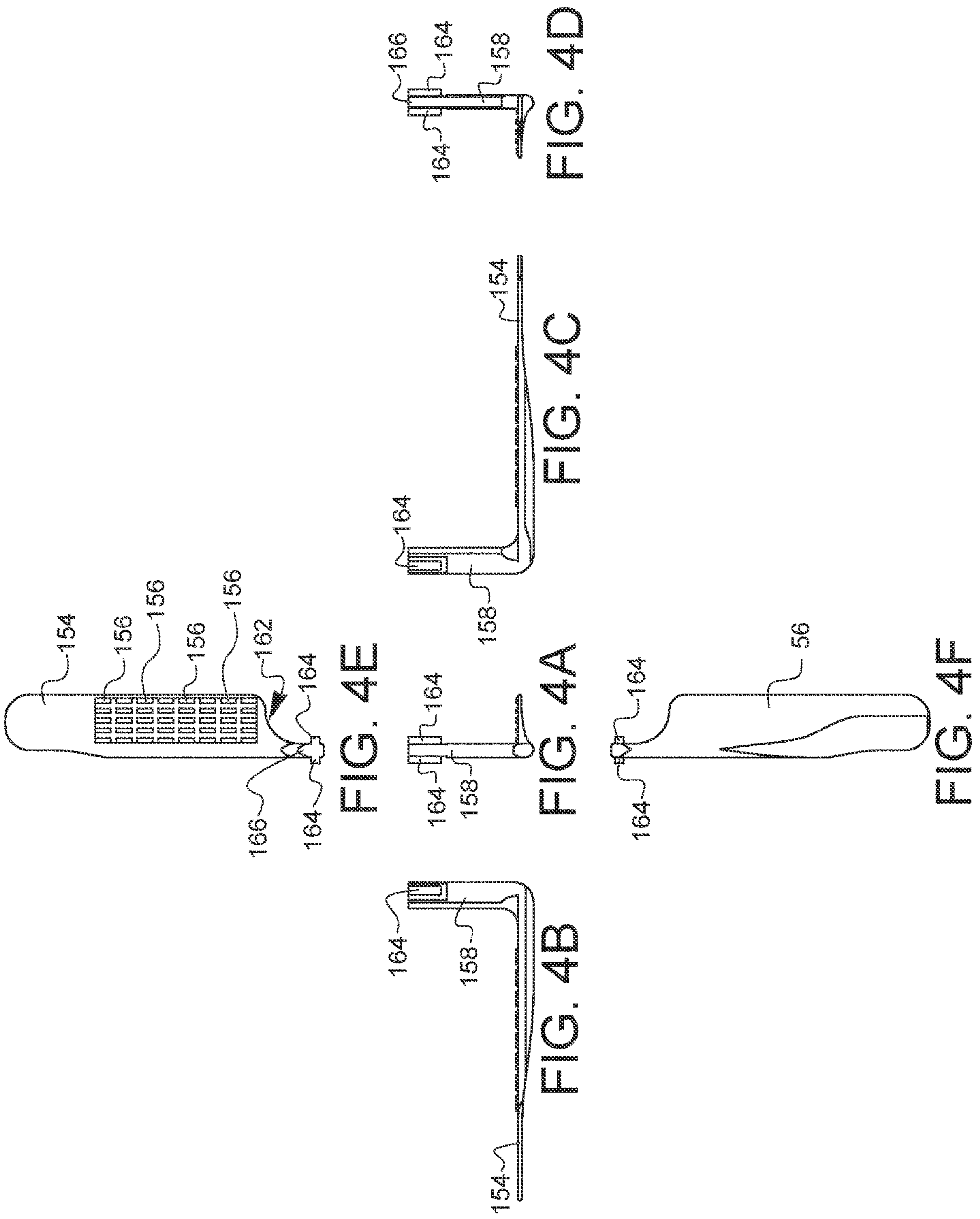
FIGS. 4A, 4B, 4C, 4D, 4E, and 4F are front, left side, right side, rear, top, and bottom elevational views, respectively, of the sternal ascender of FIG. 3.

FIG. 3 is a perspective view of a left sternal ascender. This view illustrates the various features defined by the left sternal ascender 152. The left sternal ascender 152 defines a panel 154 having several textural features 156, a contralateral, or pertaining to the opposite side of targeted anatomical area, notch 162 at a proximal end 152P, a support beam 160 traversing the underside of the panel 154, and a mounting post 158 for attachment to a sternal ascender apparatus. The panel 154 has a rounded shape with a slight edge at a distal end 152D of the panel 154 of the left sternal ascender 152. Also defined by the post 158 are two opposing alignment and orientation features 164 configured to align, slide and lock the left sternal ascender 152 into the handle. These features 164 form a general t-shape, which are configured to fit into the aforementioned t-slot on the indicator handle 22. The use of this feature will be described further in regard to FIGS. 7A-7C. The post 158 also defines an angular front alignment feature 166 which is used to help align and place the left sternal ascender in an anatomical notch defined between a rib and sternum. This can serve as a tactile assist in placing the sternal ascender in an appropriate place when in use as part of a sternal ascender apparatus. While the embodiment shown has these characteristics, alternate embodiments of a sternal ascender panel may have other shapes or radiuses, and may or may not be sharpened. Still other embodiments may have other features aside from the rectangular textural features 156 shown here, and may include other shaped features or none at all. Other embodiments of left sternal ascenders may be made of metal, plastic, composites, or mixtures or combinations thereof or contain alternate alignment or locking methods and features. FIGS. 4A, 4B, 4C, 4D, 4E, and 4F are front, left side, right side, rear, top, and bottom elevational views, respectively, of the sternal ascender of FIG. 3.

Figure 5:
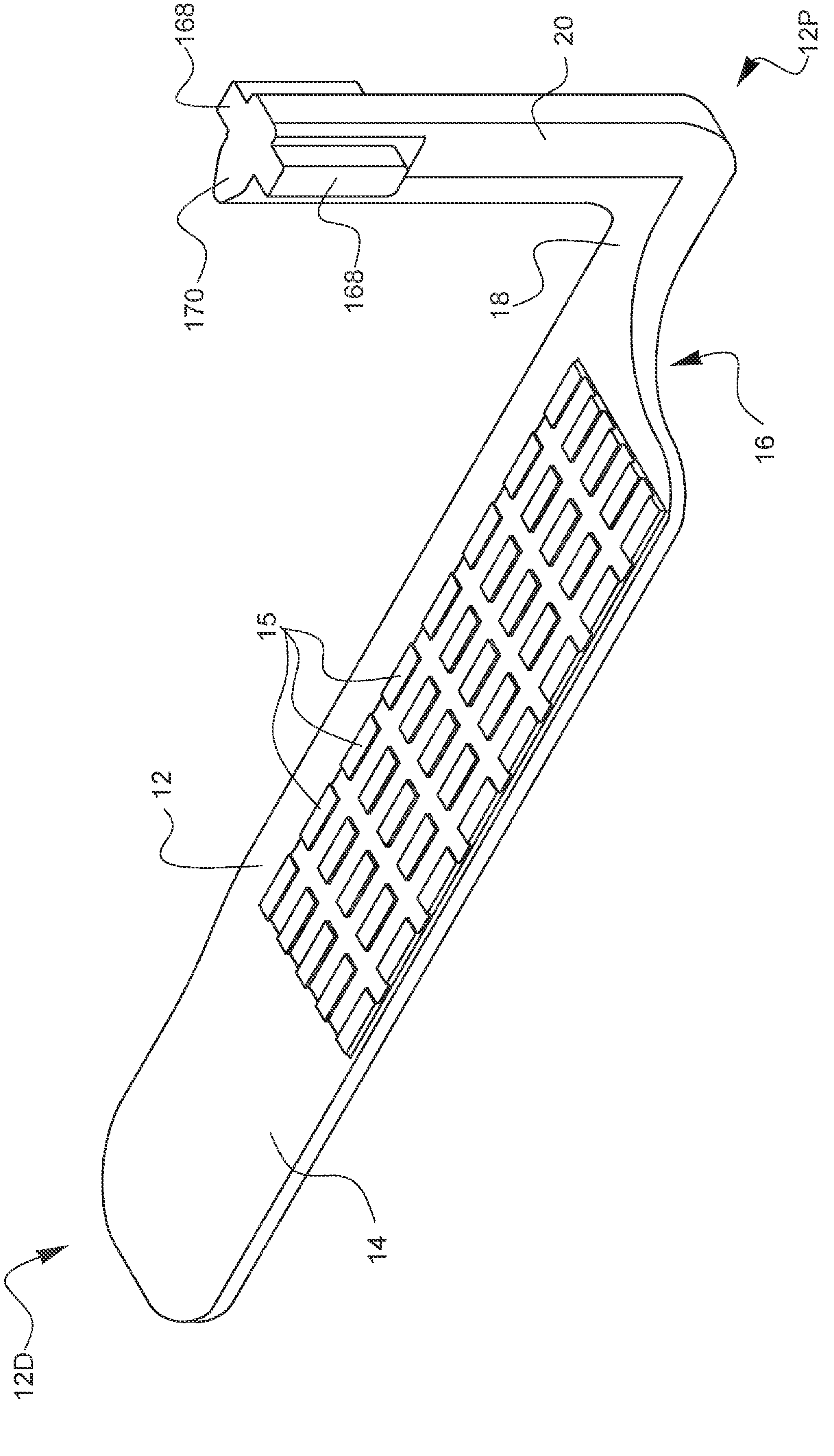
FIG. 5 is a perspective view of a right sternal ascender.
Figures 6A, 6B, 6C, 6D, 6E, 6F:
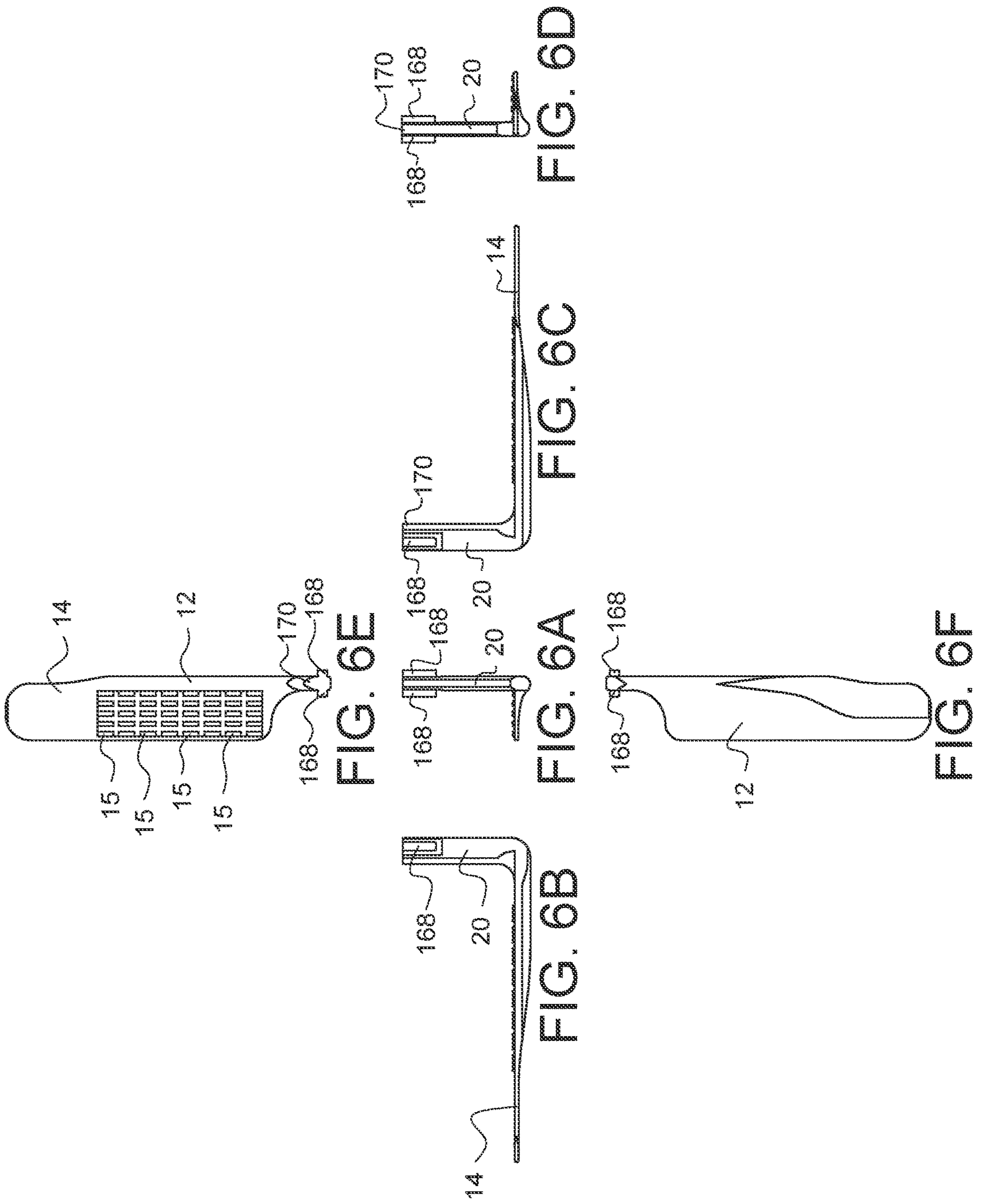
FIGS. 6A, 6B, 6C, 6D, 6E, and 6F are front, left side, right side, rear, top, and bottom elevational views, respectively, of the right sternal ascender of FIG. 5.

FIG. 5 is a perspective view of a right sternal ascender. This view illustrates the various features defined by the right sternal ascender 12. The right sternal ascender 12 defines a panel 14 having several textural features 15, a contralateral, or pertaining to the opposite side of targeted anatomical area, notch 16 at a proximal end 12P, a support beam, not shown here, traversing the underside of the panel 14, and a mounting post 20 for attachment to a sternal ascender assembly. The panel 14 has a rounded shape with a slight edge at a distal end 12D of the panel 14 of the right sternal ascender 12. Also defined by the post 20 are two opposing alignment and orientation features 168 configured to align, slide and lock the left sternal ascender 12 into the handle. These features 168 form a general t-shape, which are configured to fit into the aforementioned t-slot on the indicator handle 22. The use of this feature will be described further in regard to FIGS. 7A-7C. The post 20 also defines an angular front alignment feature 170 which is used to help align and place the left sternal ascender in an anatomical notch defined between a rib and sternum. This can serve as a tactile assist in placing the sternal ascender in an appropriate place when in use as part of a sternal ascender apparatus. While the embodiment shown has these characteristics, alternate embodiments may have other shapes or radiuses, and may or may not be sharpened. Still other embodiments may have other attachment features aside from the rectangular textural features 15 shown here, and may include other shaped features or none at all. Other embodiments of right sternal ascenders may be made of metal, plastic, composites, or mixtures or combinations thereof. FIGS. 6A, 6B, 6C, 6D, 6E, and 6F are front, left side, right side, rear, top, and bottom elevational views, respectively, of the right sternal ascender of FIG. 5.

Figure 7A:
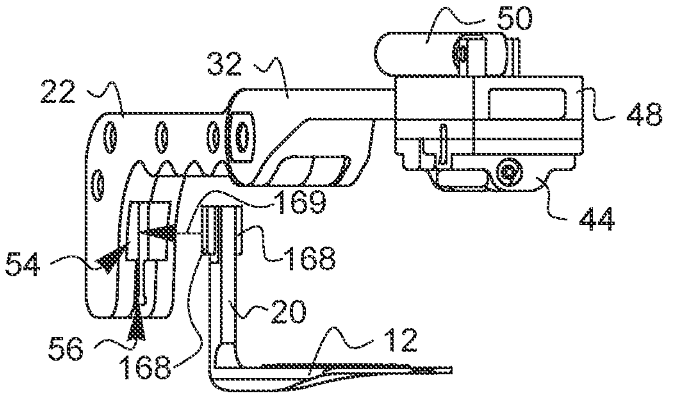
FIGS. 7A-7C are a series of perspective views illustrating operational steps showing the loading of the left sternal ascender of FIG. 5 into the sternal ascender apparatus of FIG. 1.
Figure 7B:
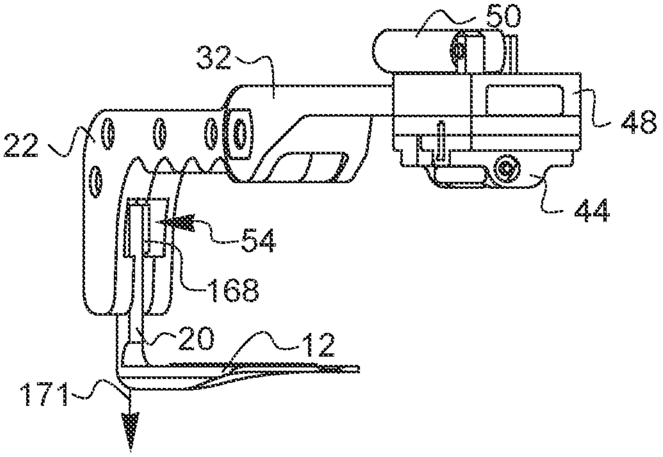
Figure 7C:
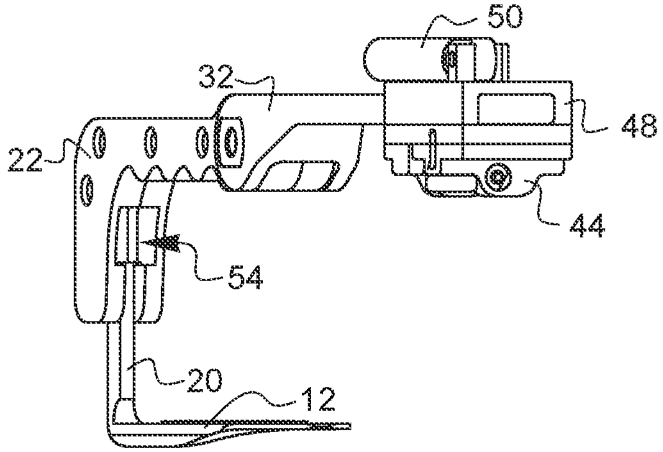

FIGS. 7A-7C are a series of perspective views illustrating operational steps showing the loading of the left sternal ascender of FIG. 5 into the sternal ascender apparatus of FIG. 1. The appropriate sternal ascender, left or right, is selected depending on the area of interest for a minimally invasive surgical procedure requiring the sternum of a patient to be lifted upward. FIG. 7A shows the right sternal ascender 12 aligned with and in proximity to the t-slot 54 of the indicator handle 22 of the sternal elevator apparatus 10 with the orientation features 168 on the post 20 of the right sternal ascender 12 moved towards direction 169 and fully inserted into the slot 54 of the indicator handle 22. Once inserted, as shown in FIG. 7B, the right sternal ascender 12 is pulled downward in direction 171 towards the seat 56 in the slot 54 of the indicator handle 22 to lock the right sternal ascender 12 into place. FIG. 7C shows the fully inserted and locked right sternal ascender 12 in the indicator handle 22.

Figure 8:
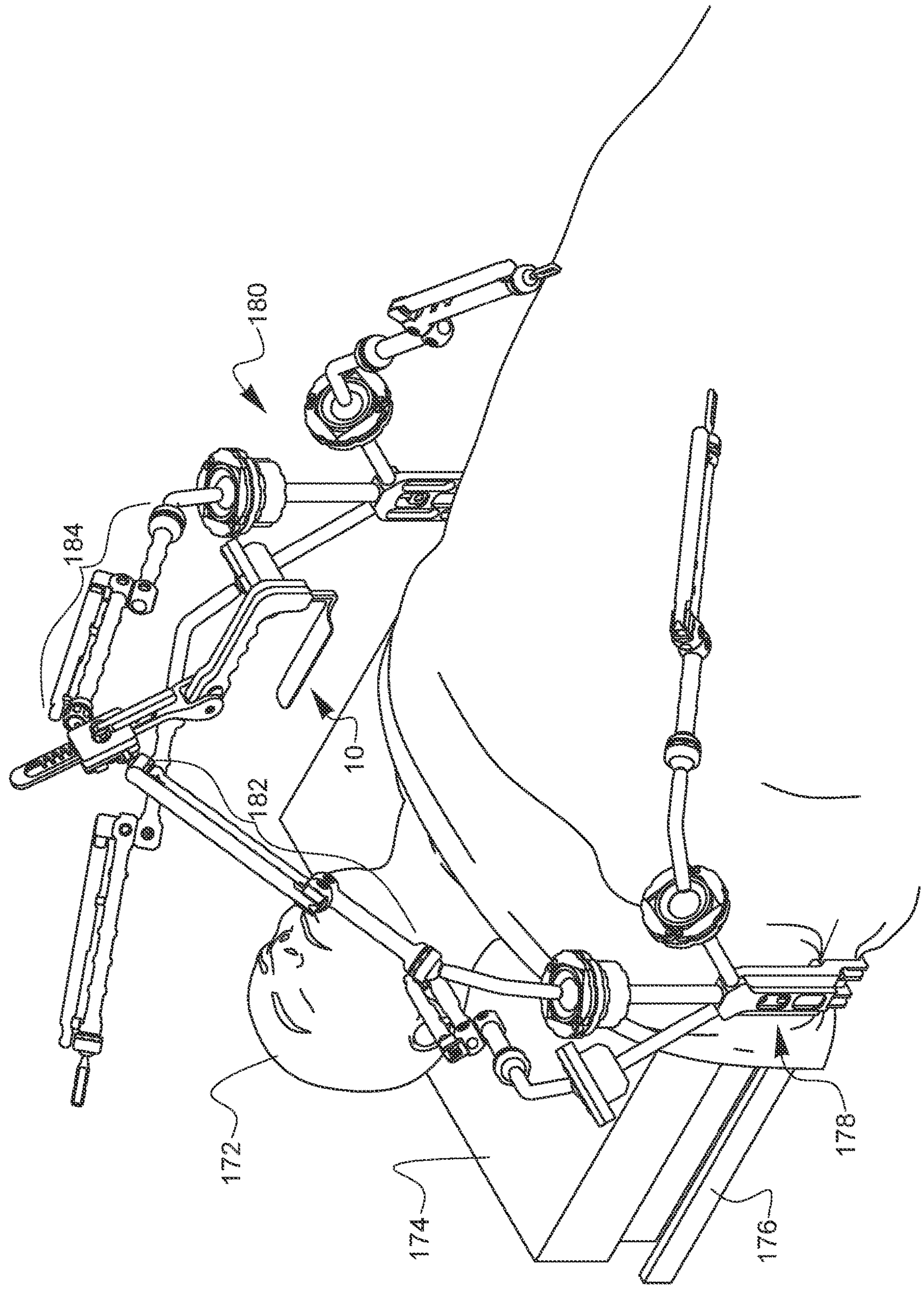
FIG. 8 is a perspective view of a surgical setting including the use of the sternal ascender apparatus of FIG. 1.

FIG. 8 is a perspective view of a surgical setting including the use of the sternal ascender apparatus of FIG. 1. In the illustrated surgical setting, an operating table 174 having a rail 176 and a patient 172 on the table 174 prepared for a surgical procedure are shown. Positioned on the rail 176 is a first surgical equipment holder apparatus 178 having a first central surgical equipment holder 182 attached to the first surgical equipment holder apparatus 178. The first surgical equipment holder apparatus 178 is attached to the sternal ascender apparatus 10 at the first adapter channel 46 formed in the dual side instrument adapter 44. On an opposite side of the table, a second surgical equipment holder apparatus 180 is attached to an opposite rail, which is not visible here. The second surgical equipment holder apparatus 180 has a second central surgical equipment holder 184 attached thereto and is also attached to the corresponding second adapter channel formed in the dual side instrument adapter 44 on its opposite side, not visible here. Each of the first central surgical equipment holder 182 and the second central surgical equipment holder 184 can be utilized to position and hold one or more pieces of surgical equipment or tools such as the sternal ascender apparatus 10 or alternatively scope holders, cannulas, or other surgical implements during a minimally invasive or other surgical procedure. In this configuration, the first central surgical equipment holder 182 and the second central surgical equipment holder 184 are shown bridging over the patient 172 in order to firmly position the sternal ascender apparatus 10 in an initial centralized location relative to the patient 172 on the table 174.

Figure 9A:
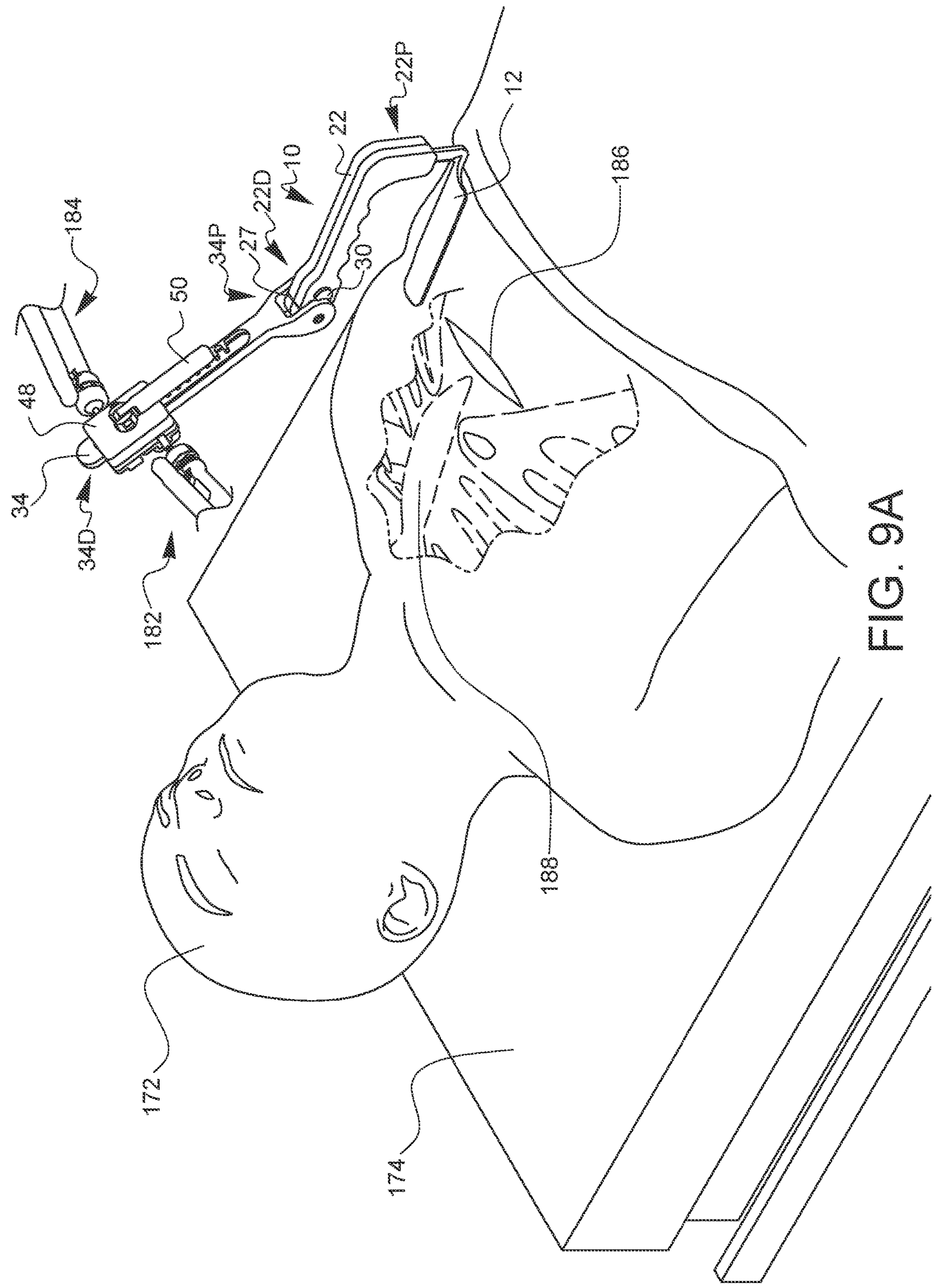
FIGS. 9A-9D are a series of perspective views illustrating operational steps of the use of the sternal ascender apparatus in a surgical context.
Figure 9B:
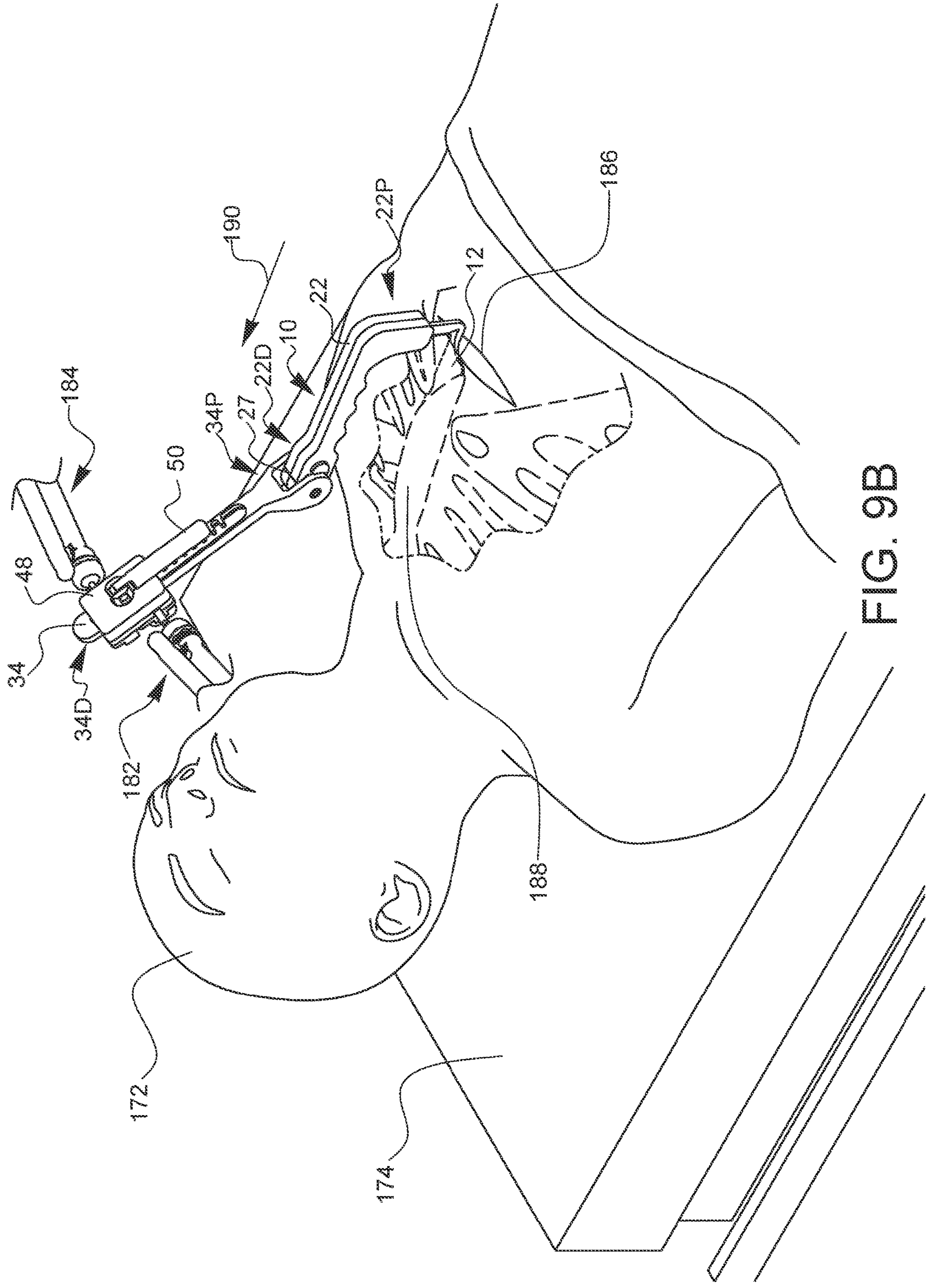
Figure 9C:
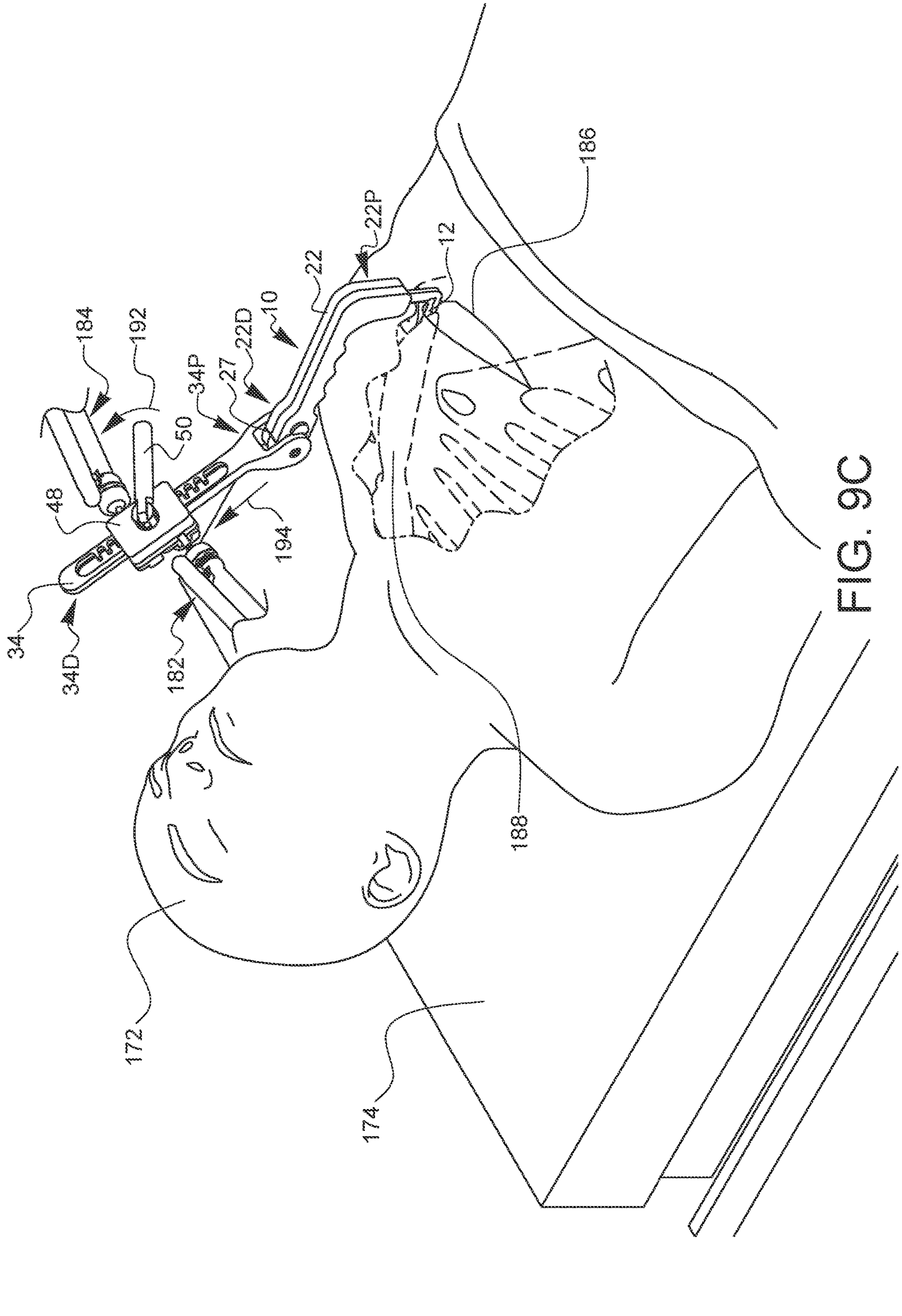
Figure 9D:
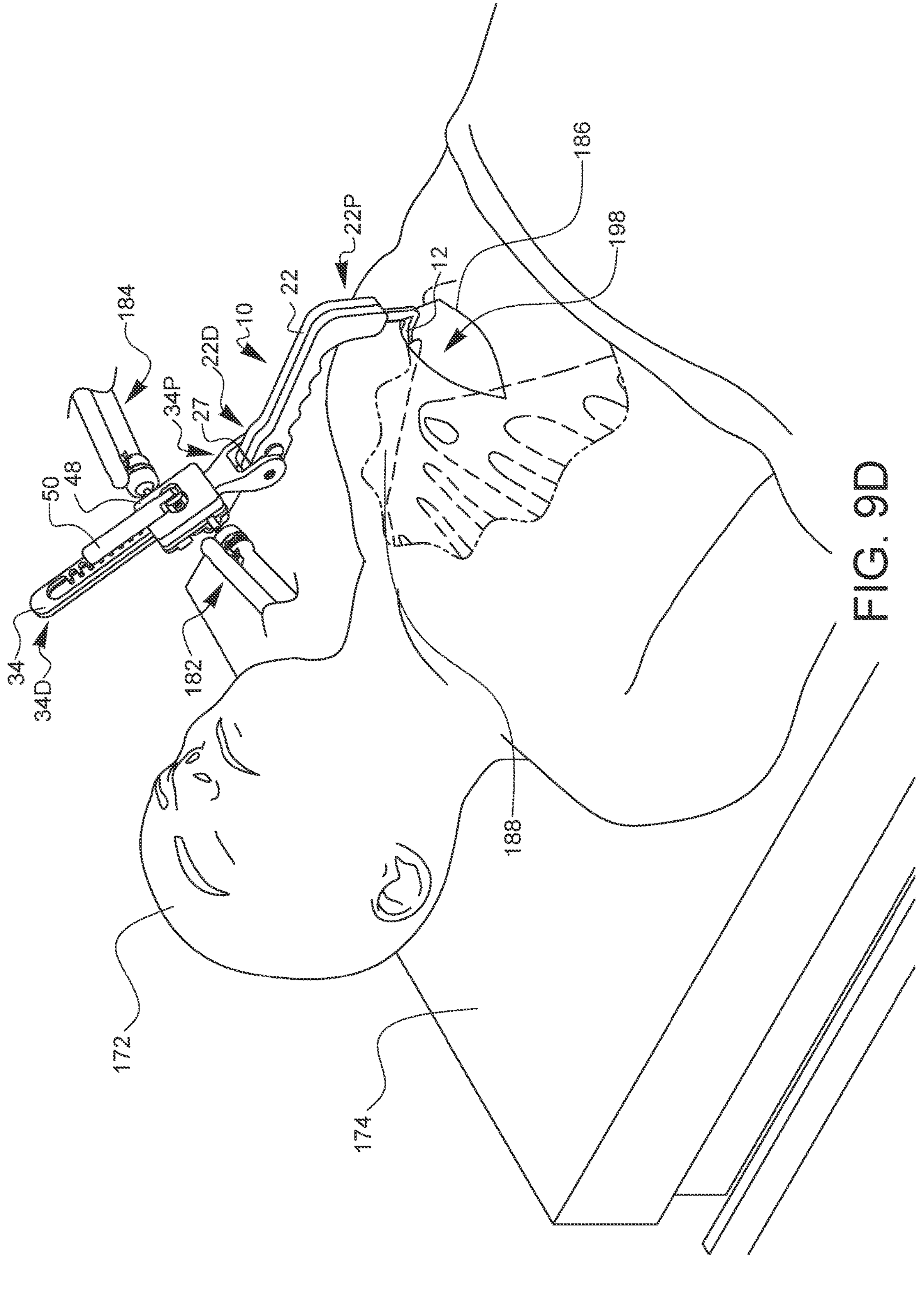

FIGS. 9A-9D are a series of perspective views illustrating operational steps of the use of the sternal ascender apparatus in a surgical context. In FIGS. 9A-9D, portions of the patient 172 are shown in cross-section and portions of various instrumentation are removed from view for the purposes of clarity. The patient 172 is shown prepped for a surgical procedure, having an incision 186 made at just below the xiphoid process at the sternal notch, near the sternum 188. The sternal elevator apparatus 10 is secured onto the first central surgical equipment holder 182 and the second central surgical equipment holder 184, which are firmly mounted onto the operating table 174. The upper rack housing 48, or the arch keystone is at the top of the toothed linear rack and thus enables subsequent movement of the rack 34 upward. The angle of the indicator handle 22 and therefore the sternal ascender 12 has been adjusted by pressing the pivot button or pressable switch 30 on the indicator handle 22, allowing movement of the indicator handle 22 relative to the linear actuator gear 34. As shown in FIG. 9B, the distal end 12D of the sternal ascender 12 is inserted in direction 190 into the incision 186 until the sternal ascender 12 is in a desired location along the sternum 188. The sternal ascender 12 is aligned with the anatomy of the sternum 188 by using the depth indicator 27 to gauge the location of the tip of the panel of the sternal ascender 12 within the chest. At this point, the first central surgical equipment holder 182 and the second central surgical equipment holder 184 are locked and secured into place after proper adjustment. FIG. 9C illustrates the swivel bar 50 being unlocked and moved counterclockwise 192 to raise the sternal ascender 12 and indicator handle 22 in direction 194, which applies retraction to the sternum 188 and creates the subxiphoid space 198 for access. A final state of this described procedure is illustrated in FIG. 9D, at which time the swivel bar 50 can be moved to a full up or down position to lock the gear housing 48 in place to prevent any further movement of the sternal ascender 12.

Figure 10A:
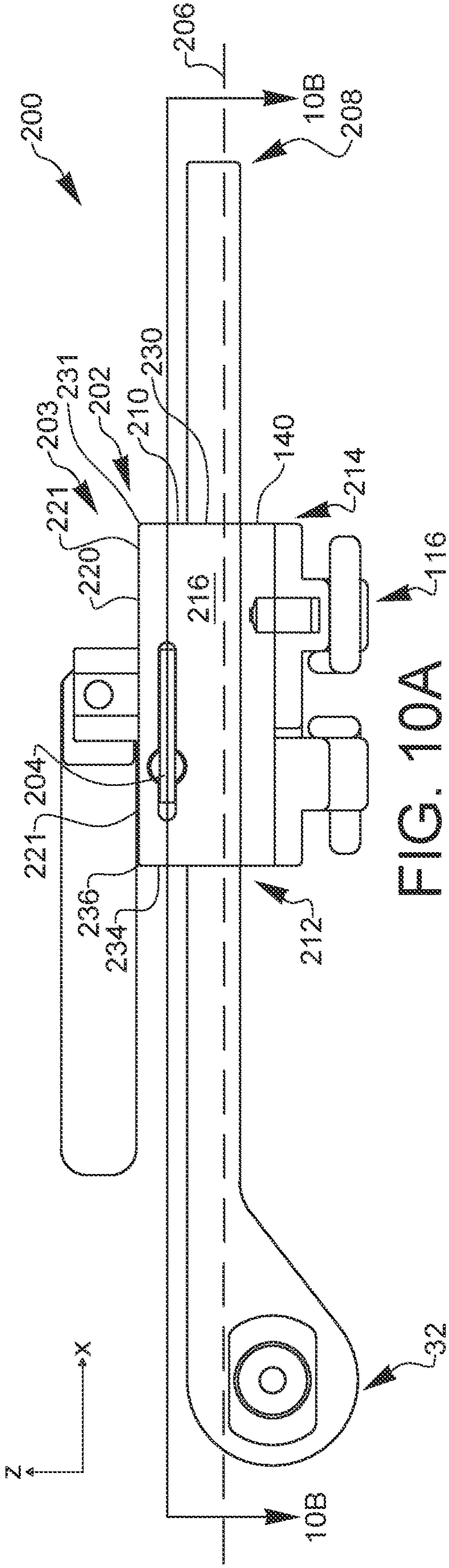
FIG. 10A is a side view of a portion of an embodiment of a sternal ascender apparatus having rack housing that includes a locking apparatus.
Figure 10B:
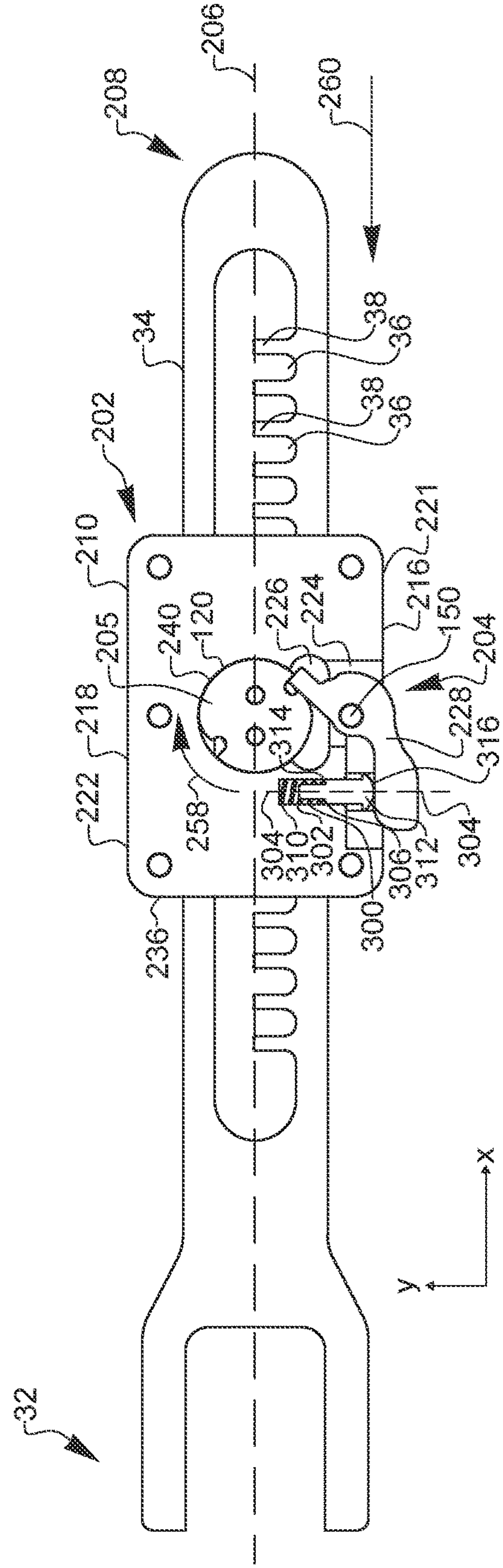
FIG. 10B is a section view of the portion of the embodiment of the sternal ascender apparatus of FIG. 10A taken along section line 10B-10B.

FIGS. 10A to 12 illustrate a further embodiment of a sternal ascender apparatus 200 having an embodiment of a dual side instrument adapter 202 that may be identical to the dual side instrument adapter 44 previously described, except that the dual side instrument adapter 202 includes a locking mechanism 204 configured to selectively engage a portion of an embodiment of a cylinder gear 205 (illustrated in the sectional view of FIG. 10B) to allow rotation of the cylinder gear 205 in a second rotational direction (arrow 256 in FIG. 11B) and to prevent rotation of the cylinder gear 205 in a first rotational direction (arrow 258 in FIG. 10B). Accordingly, displacement of the linear actuator gear 34 relative to the dual side instrument adapter 202 may be allowed in a second linear direction (arrow 262 in FIG. 11B) and may be prevented in a first linear direction (arrow 260 in FIG. 10B).

Figure 12:
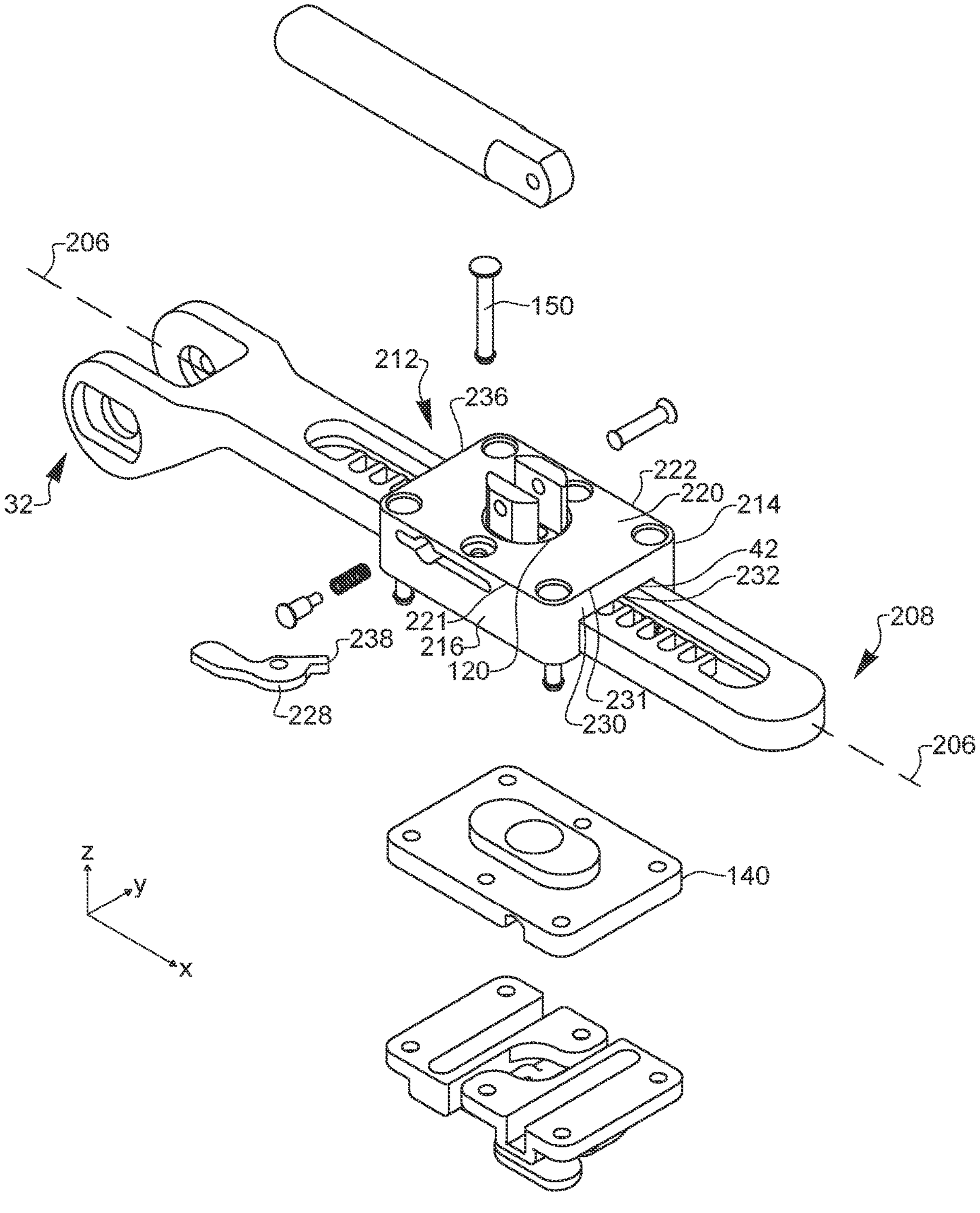
FIG. 12 is an exploded perspective view of the embodiment of the sternal ascender apparatus of FIG. 10A.

Turning to FIGS. 10A and 12, which are a front view of a portion of the sternal ascender apparatus 200 and a perspective partially-exploded view of the portion of the sternal ascender apparatus 200, respectively, a portion of the linear actuator gear 34 may extend through the actuator slot 42 of the dual side instrument adapter 202, and the dual side instrument adapter 202 may be coupled to the linear actuator gear 34 in the manner previously described. The linear actuator gear 34 may extend along an actuator axis 206 from the connection end 32 to a free end 208, and the actuator axis 206 may be parallel to the X-axis of the reference coordinate system provided in FIG. 10A. As previously explained, and as illustrated in FIG. 10B, the linear actuator gear 34 may have a plurality of teeth 36 that each extend normal or substantially normal to the actuator axis 206, and the plurality of teeth 36 may cooperate to define a plurality of recesses 38. Each of the plurality of recesses 38 may be disposed between a pair of adjacent teeth 36 of the plurality of teeth 36.

With reference to FIG. 10A, the dual side instrument adapter 202 may include a rack housing 203, which may be an assembly of an embodiment of an upper rack housing 210 and the middle rack housing 140, that may extend along the actuator axis 206 from a first end 212 to a second end 214. However, in some embodiments, the rack housing 203 may include more, or fewer, components. The linear actuator gear 34 may be displaceable relative to the dual side instrument adapter 202 (or the rack housing 203) along the actuator axis 206. However, one having ordinary skill in the art would recognize that the dual side instrument adapter 202 (or the rack housing 203) may also be displaceable relative to the linear actuator gear 34 along the actuator axis 206 if the linear actuator gear 34 is fixed.

Turning to the rack housing 203 of the dual side instrument adapter 202 in more detail, and still referring to FIG. 10A, the upper rack housing 210 may include an upper surface 220 that may extend from the first end 212 to the second end 214, and the upper surface 220 may be defined by a first lateral edge 221 that may be parallel to the actuator axis 206 but offset from the actuator axis 206 in a first direction. The upper surface 220 may also be defined by a second lateral edge 222 (illustrated in FIG. 12) that may be parallel to the actuator axis 206 but offset from the actuator axis 206 in a second direction. The upper surface 220 may extend or generally extend along the X-axis of the reference coordinate system of FIGS. 10A and 10B. In some embodiments, the upper surface may be planar or generally planar, and may extend parallel or substantially parallel to a plane defined by the X-axis and the Y-axis (i.e., the X-Y plane) of the reference coordinate system provided in FIGS. 10A and 10B.

As illustrated in FIG. 10B, the upper rack housing 210 may have a first lateral surface 216 extending from the first lateral edge 221 of the upper surface 220 towards the middle rack housing 140, and the first lateral surface 216 may extend from the first end 212 to the second end 214 of the upper rack housing 210. The upper rack housing 210 may also include a second lateral surface 218 extending from the second lateral edge 222 of the upper surface 220 towards the middle rack housing 140, and the second lateral surface 218 may extend from the first end 212 to the second end 214 of the upper rack housing 210. The first lateral surface 216 and the second lateral surface 218 may each extend (or generally extend) along the Z-axis of the reference coordinate system provided in FIG. 10A. In some embodiments, the first lateral surface 216 and the second lateral surface 218 may each be planar or substantially planar, and each of the first lateral surface 216 and the second lateral surface 218 may extend parallel or substantially parallel to a plane defined by the X-axis and the Z-axis (i.e., the X-Z plane) of the reference coordinate system provided in FIGS. 10A and 10B.

Referring to FIG. 12, the upper rack housing 210 may also include a first transverse surface 230 extending from a first transverse edge 231 of the upper surface 220 towards the middle rack housing 140, and the first transverse surface 230 may extend from the first lateral surface 216 to the second lateral surface 218. The first transverse surface 230 may extend (or generally extend) along the Z-axis of the reference coordinate system provided in FIG. 10A. In some embodiments, the first transverse surface 230 may be planar or substantially planar and may extend parallel or substantially parallel to a plane defined by the Y-axis and the Z-axis (i.e., the Y-Z plane) of the reference coordinate system provided in FIGS. 10A and 10B. In some embodiments, a first end 232 of the actuator slot 42 may extend through the first transverse surface 230.

As illustrated in FIG. 10A, the upper rack housing 210 may also include a second transverse surface 234 extending from a second transverse edge 236 of the upper surface 220 towards the middle rack housing 140, and the second transverse surface 234 may extend from the first lateral surface 216 to the second lateral surface 218. The second transverse surface 234 may extend (or generally extend) along the Z-axis of the reference coordinate system provided in FIG. 10A. In some embodiments, the second transverse surface 234 may be planar or substantially planar and may extend parallel or substantially parallel to the Y-Z plane of the reference coordinate system provided in FIGS. 10A and 10B. In some embodiments, a second end (not visible) of the actuator slot 42 may extend through the second transverse surface 234.

Referring to the cross-section view of the upper rack housing 210 of FIG. 10B, a pawl channel 224 may be formed in any suitable surface or surfaces of the upper rack housing 210 to extend inwardly towards the central opening 120 and to allow at least a portion of a limiting pawl 228 to be disposed within the pawl channel 224 and to allow an engagement portion 238 (see FIG. 12) of the limiting pawl 228 to selectively engage a portion of the cylinder gear 205 in a manner that will be described in more detail below. The pawl channel 224 may open into an interior volume 226 that extends to the central opening 120. For example, the pawl channel 224 may extend inwardly from the first lateral surface 216 towards the actuator axis 206. The limiting pawl 228 may be disposed at least partially within the pawl channel 224 and/or the interior volume 226.

As previously explained, the sternal ascender apparatus 200 may also include the cylinder gear 205 that is rotatably coupled to a portion of the rack housing 203, and FIGS. 14A to 14H provide various views of the cylinder gear 205. The cylinder gear 205 may be similar or identical to the embodiment of the cylinder gear 122 previously disclosed, but the cylinder gear 205 may include a first locking notch 241*a* that will be described in more detail below.

Figures 14A, 14B, 14C, 14D, 14E, 14F, 14G, 14H, 14I:
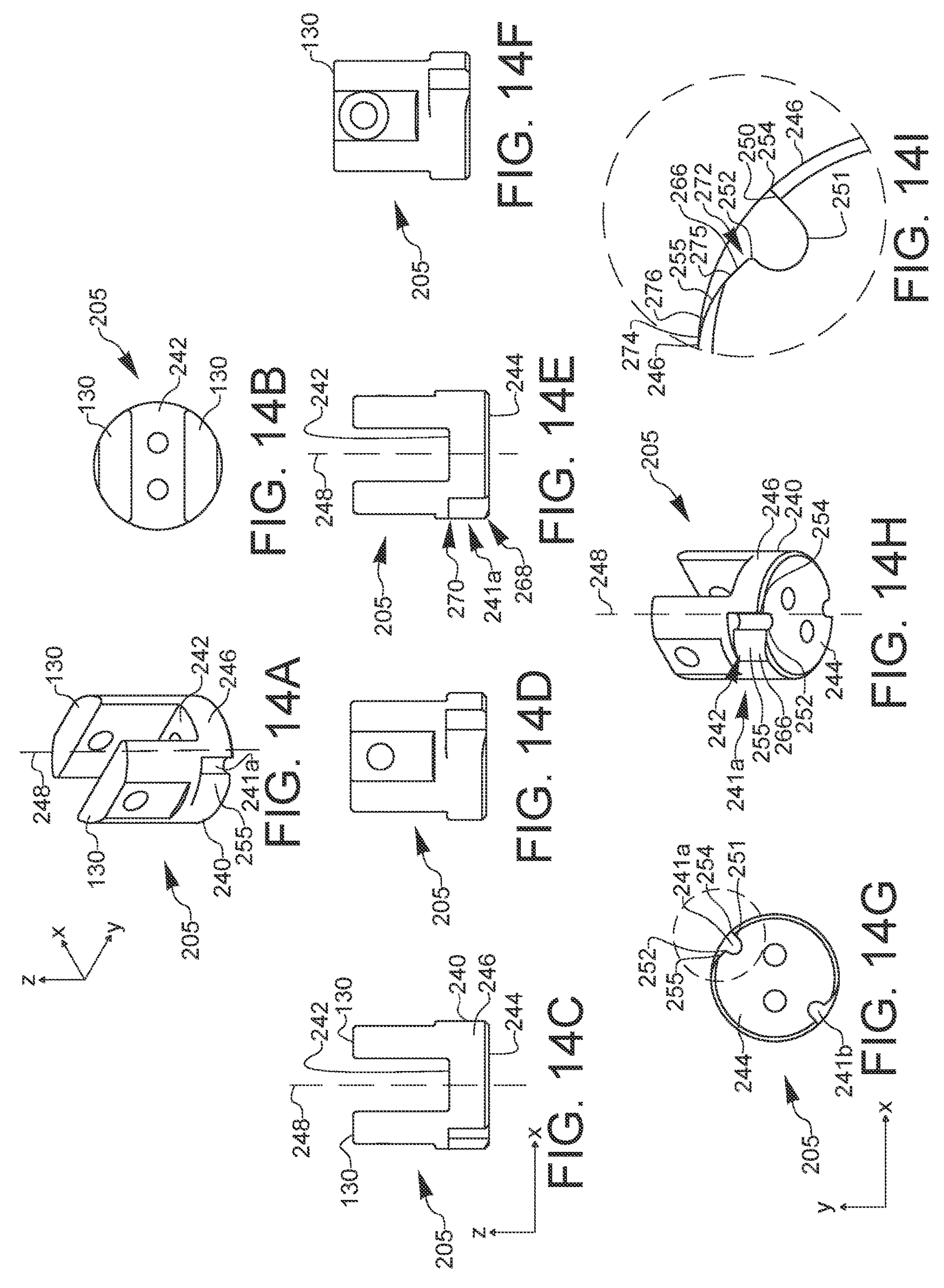
FIG. 14A to 14I are various views of an embodiment of a cylinder gear of the embodiment of the sternal ascender apparatus of FIG. 10A.

Referring to FIG. 14A, the cylinder gear 205 includes a base portion 240, and at least a portion of the base portion 240 may be disposed within the central opening 120 (as illustrated in FIG. 10B) such that the surface or surfaces that define central opening 120 constrain the base portion 240 and prevents lateral movement of the base portion 240 relative to the rack housing 203 while allowing the cylinder gear 205 to freely rotate about a gear axis 248 that is parallel to the Z-axis of the reference coordinate system of FIG. 14A.

Turning to FIG. 14C, the base portion 240 includes a first surface 242 that extends normal to or substantially normal to a gear axis 248. Each of the two sides 130 of the cylinder gear 205 extends upwardly from the first surface 242 in a direction along the gear axis 248. The base portion 240 also includes a second surface 244 that extends normal to or substantially normal to a gear axis 248, and the second surface 244 may be planar or substantially planar. Each of the two posts 126 (one of which is illustrated in FIG. 2C) may extend downwardly from the second surface 244 in a direction along the gear axis 248. The base portion 240 may further include a circumferential surface 246 that extends between the first surface 242 and the second surface 244 in a direction along the gear axis 248, and the circumferential surface 246 may be substantially cylindrical such that the base portion 240 has the shape of a disc.

With reference to the bottom view of the cylinder gear 205 of FIG. 14G, the locking mechanism 204 may include the first locking notch 241*a* that may be formed or disposed on the circumferential surface 246 of the base portion 240 of the cylinder gear 205. The first locking notch 241*a* may be any feature or features formed on or in the circumferential surface 246 that allow the engagement portion 238 of the limiting pawl 228 to (a) contact a portion of the first locking notch 241*a* when the cylinder gear 205 rotates in a first rotational direction about the gear axis 248 and (b) not contact the portion of the first locking notch 241*a* when the cylinder gear 205 rotates in a second rotational direction about the gear axis 248. So configured, the selective engagement of the engagement portion 238 of the limiting pawl 228 with the first locking notch 241*a* (or the portion of the first locking notch 241*a*) prevents further rotation of the base portion 240 of the cylinder gear 205 in the first rotational direction (arrow 258 in FIG. 10B) and preventing further displacement of the linear actuator gear 34 in the first linear direction (arrow 260 in FIG. 10B) while allowing rotation of the base portion 240 of the cylinder gear 205 in the second rotational direction (arrow 256 in FIG. 11B) and allowing displacement of the linear actuator gear 34 in the second linear direction (arrow 262 in FIG. 11B).

More particularly, as illustrated in FIG. 14G and the detail view of FIG. 14I, the first locking notch 241*a* may be at least partially defined by a curved edge 251 that extends from a first portion 252 of the circumferential surface 246 to a second portion 254 of the circumferential surface 246. The curved edge may form an arc or segment of a circle or a substantially circular shape, and the curved edge 251 may be extruded in a direction along the gear axis 248 to form the first locking notch 241*a*. In particular, with reference to FIGS. 14E and 14G, the curved edge 251 may be extruded in the direction along the gear axis 248 from a first end 268 at the second surface 244 of the base portion 240 to a second end 270 at or adjacent to the plane formed by the first surface 242 of the base portion 240. The shape of the first locking notch 241*a* may be constant or substantially constant along the entire length of the first locking notch 241*a* (i.e., along the entire length of the gear axis 248 between the first end 268 and the second end 270 of first locking notch 241*a*).

As illustrated in FIG. 14I, the locking mechanism 204 may also include a ramp portion 255 formed on or along the circumferential surface 246 that inwardly inclines or slopes from a first end 272 that intersects the first portion 252 of the circumferential surface 246 to a second end 274 that intersects a point on the circumferential surface 246. The circumferential surface 246 may be defined in part by an edge 275 that may be extruded in a direction along the gear axis 248 from the first end 268 of the first locking notch 241*a* to the second end 270 of the first locking notch 241*a* to form a ramp surface 266. The shape of the ramp portion 255 may be constant or substantially constant along the entire length of the first locking notch 241*a* (i.e., along the entire length of the gear axis 248 between the first end 268 and the second end 270 of first locking notch 241*a*). The ramp portion 255 (i.e., the ramp surface 266 of the ramp portion 255) may be configured to guide the engagement portion 238 of the limiting pawl 228 into engagement with the portion (i.e., an overhang portion 250) of the first locking notch 241*a* when the base portion 240 rotates in the first rotational direction, thereby preventing further rotation of the base portion 240 of the cylinder gear 205 in the first rotational direction and preventing further displacement of the linear actuator gear 34 in the first linear direction. However, when the base portion 240 rotates in the second rotational direction, the engagement portion 238 of the limiting pawl 228 glides long the circumferential surface 246 of the base portion 240 and "drops off" the second portion 254 of the circumferential surface 246 into the void created by the first locking notch 241*a* and eventually travels along the ramp portion 255 back into engagement with the circumferential surface 246 such that rotation in the second rotational direction continues unimpeded, and displacement of the linear actuator gear 34 in the second linear direction is allowed along the length of the linear actuator gear 34.

The base portion 240 of the cylinder gear 205 may have any suitable number of locking notches. In some embodiments, the base portion 240 of the cylinder gear 205 may have a single first locking notch 241*a*. In other embodiments, such as that illustrated in FIGS. 14A to 14I, the base portion 240 of the cylinder gear 205 may include the first locking notch 241*a* and a second locking notch 241*b*, and the second locking notch 241*b* may be disposed at any suitable location along the circumferential surface 246. For example, the second locking notch 241*b* may be disposed 180 degrees from first locking notch 241*a* along the circumferential surface 246. The second locking notch 241*b* may be oriented such that the ramp portion 255 guides the engagement portion 238 of the limiting pawl 228 into engagement with the overhang portion 250 of the second locking notch 241*b* when the base portion 240 rotates in the first rotational direction, and such that when the base portion 240 rotates in the second rotational direction, the engagement portion 238 of the limiting pawl 228 glides long the circumferential surface 246 of the base portion 240 and "drops off" the second portion 254 of the circumferential surface 246 to allow rotation in the second rotational direction to continue unimpeded.

Figures 13A, 13B, 13C:
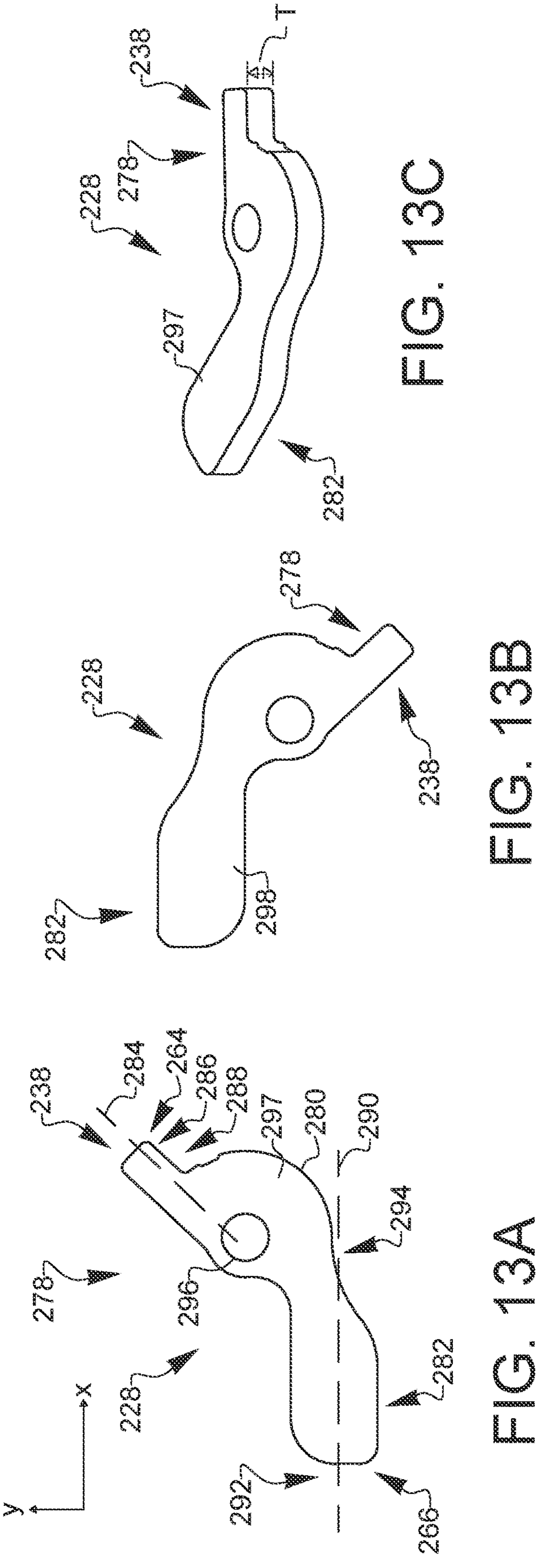
FIG. 13A to 13C are various views of an embodiment of a limiting pawl of the embodiment of the sternal ascender apparatus of FIG. 10A.

The locking mechanism 204 may further include the limiting pawl 228, and various views of the limiting pawl 228 are provided in FIGS. 13A to 13C. With reference to FIG. 13A, the limiting pawl may be elongated and may extend from a first end 264 to a second end 266, and the engagement portion 238 of the limiting pawl 228 may be disposed at or adjacent to the first end 264 of the limiting pawl 228. The limiting pawl 228 may include a locking arm 278 that extends from a hub portion 280 and a release arm 282 that extends from the hub portion 280.

The locking arm 278 may extend or generally extend along a first arm axis 284 from a first end 286 to a second end 288 at or adjacent to the hub portion 280. The first end 286 of the locking arm 278 may correspond to the first end 264 of the limiting pawl 228, and the engagement portion 238 of the limiting pawl 228 may be disposed at or adjacent to the first end 286 of the locking arm 278 of the limiting pawl 228. The release arm 278 may extend or generally extend along a second arm axis 290 from a first end 294 at or adjacent to the hub portion 280 to a second end 292, and the second end 292 of the release arm 278 may correspond to the second end 266 of the limiting pawl 228. The first arm axis 284 and the second arm axis 290 may form an angle greater than 90 degrees and less than 180 degrees, such as an angle between 100 degrees and 135 degrees. The hub portion 280 may include a pivot aperture 296 configured to receive a pin, shaft, or other axle (e.g., one of the rivets 150 illustrated in FIG. 2E) to allow the limiting pawl 228 to pivot about an axis of the pin, shaft, or other axle in a manner that will be described in more detail below, and this axis may be parallel to the gear axis 248 or the Z-axis of the reference coordinate system of FIGS. 10A and 12.

The locking arm 278 may be defined by a first surface 297 that may be planar and may extend generally along the X-Y plane of the reference coordinate system of FIG. 13A, and the locking arm 278 may be further defined by a second surface 298 that may be planar and may parallel to first surface 297 and offset from the first surface 297 (along the Z-axis of the reference coordinate system of FIG. 13A) by a thickness T. The thickness T may be equal to or less than a distance between the first end 268 of the first locking notch 241*a* and the second end 270 of the first locking notch 241*a* to allow the engagement portion 238 of the limiting pawl 228 to pivot into and out of engagement with the portion (i.e., the overhang 250) of the first locking notch 241*a* when the limiting pawl 228 is pivotably coupled to a portion of the rack housing 203.

The limiting pawl 228 may be disposed on or in any suitable location of the rack housing 203. For example, with reference to FIG. 10B, the limiting pawl 228 may be coupled to the rack housing 203 (i.e., the upper rack housing 210) by the rivet 150 extending through the pivot aperture 296 of the hub portion 280 of the limiting pawl 228. So configured, the locking arm 270 (and at least a portion of the hub portion 280) are disposed within the pawl channel 224, the interior volume 226, and/or the central opening 120. The release arm 282 of the limiting pawl 228 may be partially disposed within the pawl channel 224, and a portion of the release arm 282 of the limiting pawl 228 may extend outside of or external to the pawl channel 224 (i.e., beyond the first lateral surface 216 of the upper rack housing 210). In this configuration, the second arm axis 290 of the release arm 282 may be parallel to the first lateral edge 221 of the upper rack housing 210 when the limiting pawl 228 is in an engaged position, illustrated in FIG. 10A, in which the engagement portion 238 of the limiting pawl 228 is biased into engagement or contact with the overhang portion 250 of the second locking notch 241*b* and/or into engagement with the circumferential surface 246 of the base portion 240.

Still referring to FIG. 10B, the locking mechanism 204 may also include a biasing element 300 that may be coupled to a portion of the rack housing 203 and a portion of the limiting pawl 228 to bias the engagement portion 238 of the limiting pawl 228 into engagement with the overhang portion 250 of the second locking notch 241*b* and/or into engagement with the circumferential surface 246 of the base portion 240. The biasing element 300 may include a spring 302, such as a coil spring, that may extend or generally extend along an element axis 304 from a first end 306 to a second end 308. The spring 302 may be at least partially disposed within a bore 310 formed in a portion of the rack housing 203, such as a portion of the upper rack housing 210, such that the first end 304 of the spring 302 is in contact with an end surface defining a bottom surface of the bore 310. The bore 310 may extend along the element axis 304 inwardly from the first lateral surface 216 of the rack housing 203. The element axis 304 may be normal to the axis of the rivet 150 (i.e., the pivot axis) of the limiting pawl 228 and to the actuator axis 206.

The biasing element 300 may also include a plunger 312 that may extend or generally extend along the element axis 304 from a first end 314 to a second end 316, with the first end 314 coupled to the spring 302 at or adjacent to the second end 308 of the spring 302 So configured, with the limiting pawl 228 in the engaged position illustrated in FIG. 10B, the second end 316 of the plunger 312 is biased into contact with a portion of the release arm 282, which pivots the limiting pawl 228 about the axis of the rivet 150 such that the engagement portion 238 of the limiting pawl 228 is biased into engagement or contact with the overhang portion 250 of the second locking notch 241*b* and/or into engagement with the circumferential surface 246 of the base portion 240. However, when a user presses the release arm 282 of the limiting pawl 228 in a direction towards the actuator axis 206, the limiting pawl 228 pivots into a disengaged position (illustrated in FIG. 11B) in which the biasing element 300 also allows the limiting pawl 228 to pivot about the axis of the rivet 150 such that the engagement portion 238 of the limiting pawl 228 is displaced away from and out of contact with the overhang portion 250 of the second locking notch 241*b* and/or the circumferential surface 246 of the base portion 240 such that the cylinder gear 205 may be freely rotated in the first rotational direction (arrow 258) without obstruction from the engagement portion 238 of the limiting pawl 228.

The biasing element 300 may include any suitable elastic element or combination of elements configured to bias the engagement portion 238 of the limiting pawl 228 into engagement or contact with the overhang portion 250 of the second locking notch 241*b* and/or into engagement with the circumferential surface 246 of the base portion 240. For example, instead of the disclosed spring 302 and plunger 312, the biasing element 300 may include an elongated leaf spring (not shown) having a first end disposed in contact with a surface or portion of the rack housing 203 and a second end in contact with a portion of the release arm 282 of the limiting pawl 228.

Figures 11A, 11B:
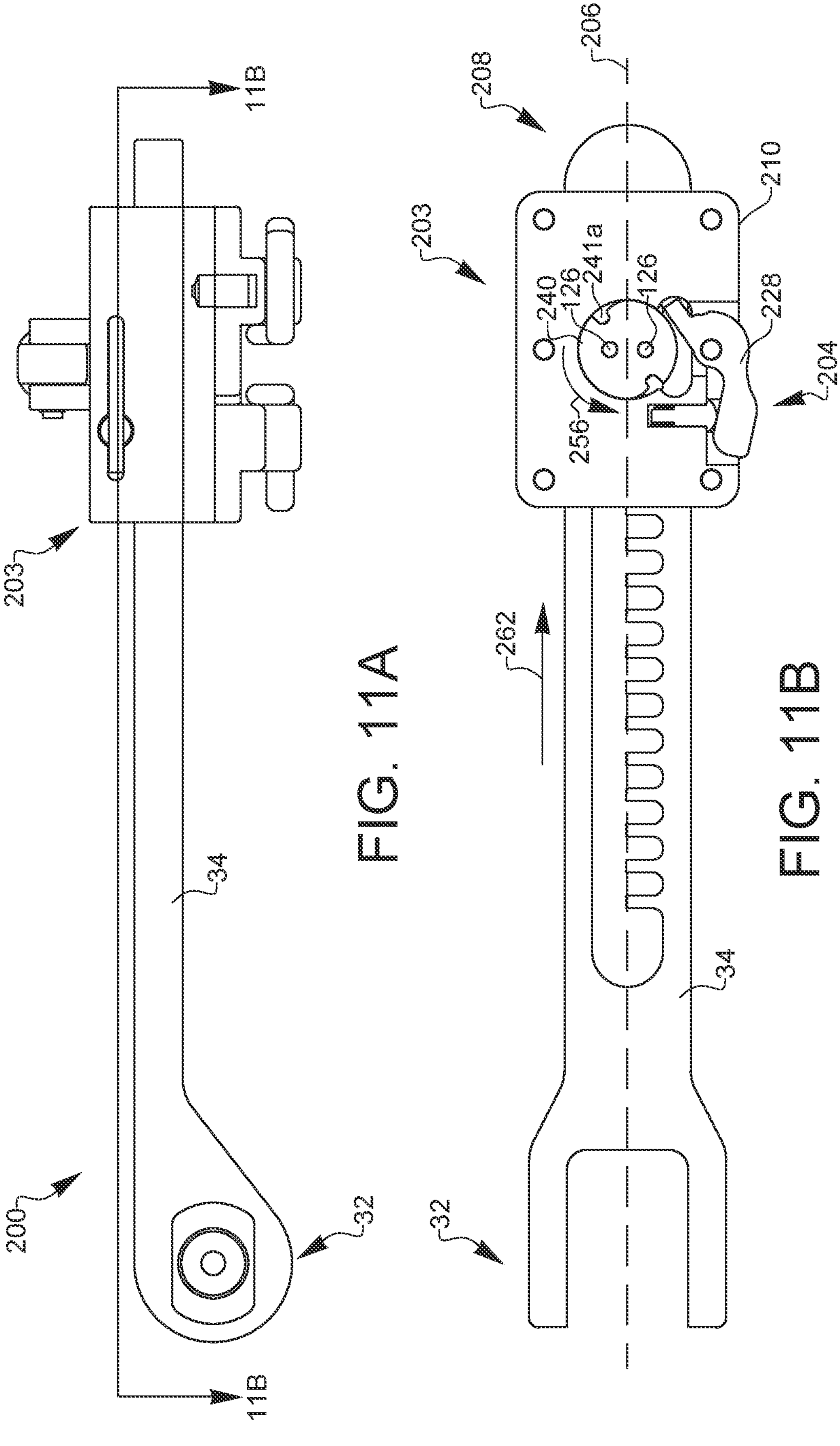
FIG. 11A is a side view of the portion of the embodiment of the sternal ascender apparatus of FIG. 10A.
FIG. 11B is a section view of the portion of the embodiment of the sternal ascender apparatus of FIG. 11A taken along section line 11B-11B.

In use, a sternal ascender 12 of the sternal ascender apparatus 200 may be inserted into an incision below the sub-xiphoid of a patient undergoing a minimally invasive surgical procedure, such as the procedure illustrated in FIG. 9B. Turning to FIG. 9C, the user may turn the swivel bar 50 in the second rotational direction (illustrated by the arrow 192) to raise the sternal ascender 12 in the second linear direction (illustrated by the arrow 194), which applies retraction to the sternum 188 and creates the subxiphoid space 198 for access. As the linear actuator gear 34 continues to move in the second linear direction to upwardly displace sternal ascender 12 (and the sternum 188), the downward resistance to the upward displacement creates a counter-force on the linear actuator gear 34 in a first linear direction (i.e., a direction opposite to the arrow 194), and this counter-force may tend to cause a rapid displacement in the first linear direction. However, as the linear actuator gear 34 begins to displace in the first linear direction relative to the rack housing 203 (with reference to FIG. 10B), the engagement portion 238 of the limiting pawl 228 of the locking mechanism 204 contact a portion of the first locking notch 241*a* of the cylinder gear 205 when the cylinder gear 205 rotates in the first rotational direction, thereby preventing further rotational displacement of the cylinder gear 204 in the first rotational direction and corresponding linear displacement of the linear actuator gear 34 in the first linear direction. If a user wishes to allow the linear actuator gear 34 to displace in the first linear direction relative to the rack housing 203, the user inwardly depresses a portion of the release arm 282 of the limiting pawl 228 to allow the cylinder gear 205 to rotate unimpeded in the first rotational direction, as previously described and as illustrated in FIG. 11B.

Various advantages of a sternal ascender assembly have been discussed above. Embodiments discussed herein have been described by way of example in this specification. It will be apparent to those skilled in the art that the foregoing detailed disclosure is intended to be presented by way of example only, and is not limiting. As just one example, although the end effectors in the discussed examples were often focused on the use of a scope, such systems could be used to position other types of surgical equipment. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. An apparatus comprising:

an elongated linear actuator gear extending along an actuator axis from a first end to a second end, the linear actuator gear having a plurality of teeth that each extend normal to the actuator axis, wherein the plurality of teeth cooperate to define a plurality of recesses, wherein each of the plurality of recesses is disposed between a pair of adjacent teeth of the plurality of teeth;

a rack housing extending along the actuator axis, wherein the rack housing is coupled to the linear actuator gear and the liner actuator gear is configured to displace along the actuator axis relative to the rack housing;

a cylinder gear comprising:

a base portion coupled to the rack housing and configured to rotate relative to the rack housing about a gear axis that is normal to the actuator axis, the base portion comprising:

a first surface;

a second surface;

a circumferential surface extending between the first surface and the second surface, wherein the circumferential surface extends in a direction parallel to the gear axis; and a first locking notch formed in the circumferential surface; and a first post extending from the first surface of the base portion such that the first post is configured to be disposed within a first of the plurality of recesses;

a second post extending from the first surface of the base portion such that the second post is configured to be disposed within a second recess of the plurality of recesses, wherein when the base portion rotates in a first rotational direction about the gear axis, the first and second posts engage a first portion of the plurality of teeth to displace the linear actuator gear in a first linear direction, and wherein when the base portion rotates in a second rotational direction about the gear axis, the first and second posts engage a second portion of the plurality of teeth to displace the linear actuator gear in a second linear direction; and an elongated limiting pawl pivotably coupled to a portion of the rack housing, the limiting pawl extending from a first end to a second end, wherein an engagement portion of the limiting pawl is disposed at or adjacent to the first end of the limiting pawl, wherein the limiting pawl is pivotable about a pivot axis between an engaged position and a disengaged position, wherein the pivot axis is disposed between the first end of the limiting pawl and the second end of the limiting pawl, the limiting pawl further comprising:

a locking arm that extends from the first end of the limiting pawl to the pivot point of the limiting pawl; and a release arm that extends from the pivot point of the limiting pawl to the second end of the limiting pawl, wherein when the base portion rotates in the first rotational direction about the gear axis, the engagement end of the limiting pawl is configured to contact a portion of the first locking notch, thereby preventing further rotation of the base portion in the first rotational direction and preventing further displacement of the linear actuator gear in the first linear direction, and when the base portion rotates in the second rotational direction about the gear axis, the engagement end of the limiting pawl is configured to not contact the portion of the first locking notch, thereby allowing rotation of the base portion in the second rotational direction and allowing displacement of the linear actuator gear in the second linear direction.

2. The apparatus of claim 1, wherein the circumferential surface of the base portion is substantially cylindrical.

3. The apparatus of claim 1, wherein the base portion has the shape of a disc.

4. The apparatus of claim 1, wherein each of the plurality of teeth extends from a first end to a second end along a tooth axis that is normal to the actuator axis, and wherein the first end of each of the plurality of teeth is aligned along a first axis parallel to the actuator axis and the second end of each of the plurality of teeth is aligned along a second axis parallel to the actuator axis and the first axis.

5. The apparatus of claim 1, the rack housing further comprising an actuator slot extending parallel to the housing axis, wherein a portion of the linear actuator gear is movably disposed within the actuator slot.

6. The apparatus of claim 1, further comprising a spring disposed between a portion of the rack housing and a portion of the second arm portion of the limiting pawl, the spring being configured to bias the engagement portion of the limiting pawl into contact with the circumferential surface of the base portion of the cylinder gear.

7. The apparatus of claim 1, wherein the pivot axis is parallel to the gear axis.

8. The apparatus of claim 1, wherein in the engaged position, the engagement end of the limiting pawl is configured to contact the portion of the first locking notch, and wherein in disengaged position, the engagement end of the limiting pawl is configured to not contact the portion of the first locking notch.

* * * * *